(12) United States Patent
Kitten et al.

(10) Patent No.: US 11,932,674 B2
(45) Date of Patent: Mar. 19, 2024

(54) MULTI SPECIFIC MOLECULES

(71) Applicant: AFFILOGIC, Nantes (FR)

(72) Inventors: Olivier Kitten, Nantes (FR); Mathieu Cinier, Nantes (FR); Simon Huet, Nantes (FR)

(73) Assignee: AFFILOGIC, Nantes (FR)

( * ) Notice: Subject to any disclaimer, the term of this patent is extended or adjusted under 35 U.S.C. 154(b) by 204 days.

(21) Appl. No.: 16/764,116

(22) PCT Filed: Nov. 13, 2018

(86) PCT No.: PCT/EP2018/081107
§ 371 (c)(1),
(2) Date: May 14, 2020

(87) PCT Pub. No.: WO2019/096797
PCT Pub. Date: May 23, 2019

(65) Prior Publication Data
US 2020/0277348 A1    Sep. 3, 2020

(30) Foreign Application Priority Data

Nov. 14, 2017 (EP) .................................. 17306580

(51) Int. Cl.
| | | |
|---|---|---|
| *A61K 38/16* | (2006.01) | |
| *C07K 14/00* | (2006.01) | |
| *C07K 14/195* | (2006.01) | |
| *C07K 14/54* | (2006.01) | |
| *C07K 16/24* | (2006.01) | |
| *C12N 15/63* | (2006.01) | |
| *A61K 39/00* | (2006.01) | |

(52) U.S. Cl.
CPC .............. *C07K 14/54* (2013.01); *A61K 38/16* (2013.01); *A61K 38/164* (2013.01); *C07K 14/195* (2013.01); *C07K 16/241* (2013.01); *C07K 16/244* (2013.01); *C12N 15/63* (2013.01); *A61K 2039/505* (2013.01); *C07K 2319/30* (2013.01)

(58) Field of Classification Search
CPC ...... A61K 38/16; A61K 38/164; C07K 14/00; C07K 14/164
See application file for complete search history.

(56) References Cited

FOREIGN PATENT DOCUMENTS

| | | | |
|---|---|---|---|
| WO | 2007139397 | A1 | 12/2007 |
| WO | 2008068637 | A2 | 6/2008 |
| WO | 2008100470 | A2 | 8/2008 |
| WO | 2012009705 | A1 | 1/2012 |

OTHER PUBLICATIONS

F. F. Miranda et al., "Reagentless fluorescent biosensors from artificial families of antigen binding proteins," Biosensors and Bioelectronics, vol. 26, 2011, pp. 4184-4190.
S. L. Moores et al., "A Novel Bispecific Antibody Targeting EGFR and cMet Is Effective against EGFR Inhibitor- Resistant Lung Tumors," Cancer Research, vol. 76, No. 13, 2016, pp. 3942-3953.
B. Mouratou et al., "Remodeling a DNA-binding protein as a specific in vivo inhibitor of bacterial secretin PulD," PNAS, vol. 104, No. 46, 2007, p. 17983-17988.
K. D. Orcutt et al., "A modular IgG-scFv bispecific antibody topology," Protein Engineering, Design & Selection, vol. 23, No. 4, 2010, pp. 221-228.
U. Reusch et al., "A tetravalent bispecific TandAb (CD19/CD3), AFM11, efficiently recruits T cells for the potent lysis of CD19 tumor cells," mAbs, vol. 7, Issue 3, 2015, pp. 584-604.
U. Reusch et al., "Characterization of CD33/CD/3 Tetravalent Bispecific Tandem Diabodies (TandAbs) for the Treatment of Acute Myeloid Leukemia," Clinical Cancer Research, vol. 22, No. 23, 2016, pp. 5829-5838.
A. Rothe et al., "A phase 1 study of the bispecific anti-CD30/CD/16A antibody construct AFM13 in patients with relapsed or refractory Hodgkin lymphoma," Clinical Trials and Observations, vol. 125, No. 26, 2017, pp. 4024-4031.
G. Schaefer et al., "A Two-in-One Antibody against HER3 and EGFR Has Superior Inhibitory Activity Compared with Monospecific Antibodies," Cancer Cell, vol. 20, 2011, pp. 472-486.
J. U. Schmohl et al., "Enhanced ADCC and NK Cell Activation of an Anticarcinoma Bispecific Antibody by Genetic Insertion of a Modified IL-15 Cross-linker," The American Society of Gene & Cell Therapy, vol. 24, No. 7, 2016, pp. 1312-1322.
B. Schneider et al., "Targeted siRNA Delivery and mRNA Knockdown Mediated by Bispecific Digoxigenin-binding Antibodies," The American Society of Gene & Cell Therapy, vol. 1, 2012, pp. 1-11.
M. Shima et al., "Factor VIII-Mimetic Function of Humanized Bispecific Antibody in Hemophilia A," The New England Journal of Medicine, vol. 374, No. 21, 2016, pp. 2044-2053.
A. M. Shukra et al., "Production of Recombinant Antibodies using Bacteriophages," European Journal of Microbiology and Immunology, vol. 4, No. 2, 2014, pp. 91-98.
B. J. Solomon et al., "A First-Time-In-Human Phase I Clinical Trial of Bispecific Antibody-Targeted, Paclitaxel- Packaged Bacterial Minicells," PLOS ONE, 2015, pp. 1-17.
C. R. Stadler et al., "Characterization of the first-in-class T-cell-engaging bispecific single-chain antibody for targeted immunotherapy of solid tumors expressing the oncofetal protein claudin 6," Oncoimmunology, vol. 5, No. 3, 2016, pp. 1-12.
M. R. Suresh et al., "Advantages of bispecific hybridomas in one-step immunocytochemistry and immunoassays," Proc. Natl. Acad. Sci. USA, vol. 83, 1986, pp. 7989-7993.
J. T. Thaden et al., "Pseudomonas aeruginosa Bacteremic Patients Exhibit Nonprotective Antibody Titers Against Therapeutic Antibody Targets PcrV and Psl Exopolysaccharide," The Journal of Infectious Diseases, vol. 213, 2016, pp. 640-648.

(Continued)

*Primary Examiner* — Xiaozhen Xie
(74) *Attorney, Agent, or Firm* — POLSINELLI PC

(57) ABSTRACT

The invention relates to proteins having multi-specific binding abilities by fusion of an OB-fold variant, in particular from the Sac7d family, to the light or heavy chain of an antibody.

20 Claims, 7 Drawing Sheets

Specification includes a Sequence Listing.

(56) References Cited

OTHER PUBLICATIONS

K. Urbanska et al., "Targeted cancer immunotherapy via combination of designer bispecific antibody and novel gene-engineered T cells," Journal of Translational Medicine, vol. 12, Issue 347, 2014, pp. 1-12.

M. Vyas et al., "Mono- and dual-targeting triplebodies activate natural killer cells and have anti-tumor activity in vitro and in vivo against chronic lymphocytic leukemia," Oncoimmunology, vol. 5, No. 9, 2016, pp. 1-14.

U. H. Weidle et al., "Tumor-Antigen-Binding Bispecific Antibodies for Cancer Treatment," Seminars in Oncology, vol. 41, No. 5, 2014, pp. 653-660.

Y. Xu et al., "Production of bispecific antibodies in "knobs-into-holes" using a cell-free expression system," mAbs, vol. 7, Issue 1, 2015, pp. 231-242.

F. Yang et al., "Bispecific Antibodies as a Development Platform for New Concepts and Treatment Strategies," International Journal of Molecular Sciences, vol. 18, No. 48, 2017, pp. 1-21.

Y. J. Yu et al., "Therapeutic bispecific antibodies cross the blood-brain barrier in nonhuman primates," Science Translational Medicine, vol. 6, Issue 261, 2014, pp. 1-10.

G. Fan et al., "Bispecific antibodies and their applications," Journal of Hematology & Oncology, vol. 8, Issue 130, 2015, pp. 1-14.

G. K. Farrington et al., "A novel platform for engineering blood-brain barrier-crossing bispecific biologics," The FASEB Journal, vol. 28, 2014, pp. 1-15.

M. Florio et al., "A bispecific antibody targeting sclerostin and DKK-1 promotes bone mass accrual and fracture repair," Nature Communications, 2016, pp. 1-14.

T. Gocha et al., "Identification and characterization of a novel Ss07dscaffold-based binder against Notch1," Scientific Reports, 2017, pp. 1-11.

Y. Huang et al., "Engineered Bispecific Antibodies with Exquisite HIV-1-Neutralizing Activity," Cell., vol. 165, No. 7, 2016, pp. 1621-1631.

H. Hurwitz et al., "A Phase I, first-in-human, open label, dose escalation study of MGD007, a humanized gpA33 X CD3 dual-affinity re-targeting (DART) protein in patients with relapsed/refractory metastatic colorectal carcinoma," Journal for ImmunoTherapy of Cancer, vol. 2, Suppl. 3, 2014, p. 86.

V. Kalichuk et al., "The archaeal "7kDa DNA-binding" proteins: extended characterization of an old gifted family," Scientific Reports, 2016, pp. 1-10.

C. Klein et al., "Progress in overcoming the chain association issue in bispecific heterodimeric IgG antibodies," mAbs, vol. 4, No. 6, 2012, pp. 653-663.

C. Klein et al., "The use of CrossMAb technology for the generation of bi- and multispecific antibodies," MABS, vol. 8, No. 6, 2016, pp. 1010-1020.

J. Kloepper et al., "Ang-2/VEGF bispecific antibody reprograms macrophages and resident microglia to anti-tumor phenotype and prolongs glioblastoma survival," PNAS, vol. 113, No. 16, 2016, pp. 4476-4481.

R. Kontermann et al., "Bispecific antibodies," Drug Discovery Today, vol. 20, No. 7, 2015, pp. 838-847.

M. Krehenbrink et al., "Artificial Binding Proteins (Affitins) as Probes for Conformational Changes in Secretin PulD," J. Mol. Biol., vol. 383, 2008, pp. 1058-1068.

R. Kunert et al., "Advances in recombinant antibody manufacturing," Appl. Microbiol. Biotechnol., vol. 100, 2016, pp. 3451-3461.

D. Lee et al., "Simultaneous blockade of VEGF and DII4 by HD105, a bispecific antibody, inhibits tumor progression and angiogenesis," MABS, vol. 8, No. 5, 2016, pp. 892-904.

A. Li et al., "A single-domain antibody-linked Fab bispecific antibody Her2-S-Fab has potent cytotoxicity against Her2- expressing tumor cells," AMB Express, vol. 6, No. 32, 2016, pp. 1-8.

J. K. H. Liu et al., "The history of monoclonal antibody development—Progress, remaining challenges and future innovations," Annals of Medicine and Surgery, vol. 3, 2014, pp. 113-116.

H. F. Liu et al., "Recovery and purification process development for monoclonal antibody production," mAbs, vol. 2, Issue 5, 2010, pp. 480-499.

J. Ma et al., "B7-H3 as a promising target for cytotoxicity T cell in human cancer therapy," Oncotarget, vol. 7, No. 20, 2016, pp. 29480-29491.

"One agent, two targets—Why industry is investing in bispecific molecules," Oncology—The Bispecific Approach, MedNous, 2016, pp. 5-7.

S. Metz et al., "Bispecific digoxigenin-binding antibodies for targeted payload delivery," PNAS, vol. 108, No. 20, 2011, pp. 8194-8199.

International Search Report and Written Opinion dated Feb. 28, 2019 for corresponding PCT Application No. PCT/EP2018/081107.

Feifan Yu et al., "An affibody-adalimumab hybrid blocks combined IL-6 and TNF-triggered serum amyloid A secretion in vivo," MABS, vol. 6 affibody-adalimumab hybrid, No. 6, 2014, pp. 1598-1607 XP055457021.

S. Brack et al., "A Bispecific HER2-Targeting FynomAb with Superior Antitumor Activity and Novel Mode of Action," Molecular Cancer Therapeutics, vol. 13, No. 8, 2014, pp. 2030-2039 XP055269387.

Annika Jarviluoma et al., "High-Affinity Target Binding Engineered via Fusion of a Single-Domain Antibody Fragment with a Ligand-Tailored SH3 Domain," PLOS ONE, vol. 7, No. 7, 2012, p. e40331 XP055457017.

Jamie B. Spangler et al., "Triepitopic Antibody Fusions Inhibit Cetuximab-Resistant BRAF and KRAS Mutant Tumors via EGFR Signal Repression," Journal of Molecular Biology, vol. 422, No. 4, 2012, pp. 532-544 XP055196617.

G. Behar et al., "Tolerance of the archaeal Sac7d scaffold protein to alternative library designs: characterization of anti-immunoglobulin G Affitins," Protein Engineering, Designa & Selection, vol. 26, No. 4, 2013, pp. 267-275.

J. Berg et al., "Bispecific antibodies that mediate killing of cells infected with human immunodeficiency virus of any strain," Proc. Natl. Acad. Sci. USA, vol. 88, 1991, pp. 4723-4727.

N. M. Biel et al., "Targeting the Angiopoietin-2/Tie-2 axis in conjunction with VEGF signal interference," Cancer Lett., vol. 380, No. 2, 2016, pp. 528-533.

S. Bournazos et al., "Bispecific anti-HIV-1 antibodies with enhanced breadth and potency," Cell., vol. 165, No. 7, 2016, pp. 1609-1620.

U. Brinkmann et al., "The making of bispecific antibodies," MABS, vol. 9, No. 2, 2017, pp. 182-212.

C. Cain et al., "Crossing over to bispecificity," Science-Business exchange, 2011, pp. 1-3.

P. Chames et al., "Bispecific antibodies for cancer therapy—The light at the end of the tunnel?" mAbs, vol. 1, Issue 6, 2009, pp. 539-547.

M. Cinier et al., "Bisphosphonate Adaptors for Specific Protein Binding on Zirconium Phosphonate-based Microarrays," Bioconjugate Chem., vol. 20, 2009, pp. 2270-2277.

J. Couch et al., "Addressing Safety Liabilities of TfR Bispecific Antibodies That Cross the Blood-Brain Barrier," Sci. Transl. Med., vol. 5, Issue 183, 2013, pp. 1-12.

A. Digiandomenico et al., "A multifunctional bispecific antibody protects against Pseudomonas aeruginosa," Sci. Transl. Med., vol. 6, Issue 262, 2014, pp. 1-12.

M. Dillon et al., "Efficient production of bispecific IgG of different isotypes and species of origincells," MABS, vol. 9, No. 2, 2017, pp. 213-230.

A.

B.

MULTI SPECIFIC MOLECULES

CROSS-REFERENCE TO RELATED APPLICATIONS

This application is a national stage application (under 35 U.S.C. § 371) of PCT/EP2018/081107, filed Nov. 13, 2018, which claims benefit of European Application No. 17306580.6, filed Nov. 14, 2017, which are incorporated herein by reference in their entireties.

SEQUENCE LISTING

This application contains a Sequence Listing submitted as an ASCII text file via EFS-Web and is incorporated herein by reference in its entirety. The ASCII text file was created on Nov. 14, 2017, is named 16764116_2_1.txt, and is 26 kilobytes in size.

FIELD OF THE DISCLOSURE

The invention is in the field of molecular biology and relates in particular to the development of novel molecules and conjugates having multiple binding specificities.

INTRODUCTION

A bispecific monoclonal antibody (Mab) is an artificial protein that can simultaneously bind to two different types of antigen. They can be manufactured in several structural formats. They are generally used for cancer immunotherapy and drug delivery.

There are different kinds of bispecific antibody formats:
The bispecific antibodies that keep the full IgG structure. These benefit from Fc-mediated effector functions, such as antibody-dependent cell-mediated cytotoxicity (ADCC), antibody-dependent cellular phagocytosis (ADCP), complement fixation, and FcRn-mediated recycling, (which is responsible for the long half-life). They contain two Fab arms and one Fc region with the two Fab sites binding different antigens. Generally, each heavy and light chain pair is from a unique mAb. These bi-specific antibodies are often manufactured with the quadroma, or the hybrid hybridoma, method.
The Fc depleted antibodies. These include chemically linked Fabs, consisting of only the Fab regions, and various types of bivalent and trivalent single-chain variable fragments (scFvs), or of fusion proteins mimicking the variable domains of two antibodies.

Full IgG bispecific antibodies can be then differentiated depending on their engineering processes leading either to a symmetrical or an asymmetrical molecule, which provides different challenges.

Asymmetrical bispecific antibodies result of an in vitro chain swapping that can be enzymatically assisted or in the fusion of different hybridomas (referred to as quadroma). However, these technologies allow the generation of the expected bispecific molecule in a mixture with a high content of undesired side products that have to be separated out. With the quadroma technology, as an example, promiscuous pairing of heavy and light chains of two antibodies expressed in one cell can theoretically result in 16 different combinations (10 different molecules), with only one being bispecific and the remaining pairings resulting in non-functional or monospecific molecules. Such process results in a statistical amount (and recovery) of the bispecific molecule of 12.5% in the solution.

The main challenge then lies in the ability to drive the correct pairing of the heavy and light chain. This has been assessed by technologies such as Knob-into-hole for the heavy chain, and technologies such as crossmab for the light chain. The implementation of these technologies makes it possible to obtain a significant decrease of the number of side-products during the generation process, but this achievement is only made possible by the insertion of many point mutations to favor the correct heavy and light chain assemblies, which is not without consequences with respect to the ability of the molecules to be further developed. In particular, such antibodies can be immunogenic, with the Fc region causing detrimental downstream immune responses Symmetrical bi-specific antibodies rely instead on the fusion of extra ScFv domains (Tandem Fab-IgG, DVD-IG, CODV-Ig . . . ) to bring additional specificity to the initial IgG. The critical issues to be considered here rely on the linker connecting the ScFv to the IgG and on the intrinsic stability of the ScFv that is connected, which might affect manufacturability and production. This is particularly true for bi-specific antibodies and becomes even more challenging when considering tri- or tetra-specific antibodies.

Bi-specific molecules and in particular antibodies can be used any time it is needed to address multiple targets on a same, parallel or different pathway. In particular, such bi-specific antibodies have been developed in cancer immunotherapy, so as to bind both the tumor cell and cytotoxic cell. Bispecific antibodies also have a higher cytotoxic potential, and bind to antigens that are expressed relatively weakly. Furthermore, targeting more than one molecule can be useful to circumvent the regulation of parallel pathways and avoid resistance to the treatment.

WO 2012/009705 relates to complexes containing one or more modular recognition domains, and cite affitins (based on Sac7d from the hyperthermophilic archaeon) as alternative scaffolds. However, this document by itself, doesn't provide any information as to the nature of the so-called affitins, in particular the specific structure of such, or any reference as to the nature of these, nor does this document actually demonstrate that any complex would properly fold and maintain activity. In summary, the teaching of this document is incomplete and speculative.

Yu et al (MAbs. 2014; 6(6):1598-607) D2 discloses adalimumab (a humanized antibody binding TNFa) fused to the affibody ZIL6 which binds IL6. Affibody molecules are antibody mimetics which consist of small proteins based on three-helix bundle domain engineered to bind target proteins with high affinity, which differ from the OB-fold domain herein disclosed. This document doesn't mention any information pertaining to yield.

Brack et al (Mol Cancer Ther. 2014 August; 13(8):2030-9) disclose a bispecific Her2-targeting fusion protein comprising an anti-Her2 antibody pertuzumab and a FynSH3-derived binding protein which are 7 kDa globular proteins derived from the SH3 domain of the human Fyn kinase.

Järviluoma et al (PLoS One. 2012; 7(7):e40331) discloses neffins which are single domain antibody fragments (llama Ig heavy chain variable domain, VHH) fused to a 57 amino acid long SH3 domain engineered to bind several proteins of interest (see abstract). The single chain neffin protein therein disclosed can't be confused with a modified antibody comprising two heavy and light chains.

Spangler et al (J Mol Biol. 2012 Sep. 28; 422(4):532-44) discloses the anti-EGFR antibody cetuximab-based fused to engineered EGFR-binding variants of the 10th type III domain of human fibronectin. These complexes are different from the complexes herein disclosed.

WO 2008/100470 discloses Ig fusion proteins, and doesn't mention the OB-fold proteins and variants herein disclosed, nor their use for the production of modified antibodies.

It thus remains to develop multi-specific molecules that would be easy to produce, with a good yield, and that would also be expected to be as stable as antibodies.

The applicant proposed to produce such molecules by creating novel artificial proteins that comprise an antibody (regular antibody or bi-specific antibody) with an OB-fold domain located at the N- or C-terminus of at least one of its heavy or light chain. The OB-fold domain is preferably fused or linked to the chain of the antibody by genetic engineering: the sequence coding for the domain is genetically fused to the 5'- and/or 3'-end of the antibody heavy and/or light chain sequence and the protein artificial protein is thus produced by introducing the modified sequence in an appropriate cell line or bacterial strain. It is to be noted that a few amino acids (linker) may be added between the antibody and the OB-fold domain.

The examples show that higher or at least similar or equal yields of the disclosed polypeptide are obtained compared to the antibody without the OB domain fused thereto. The examples show that such effect is obtained for various constructs. Since the antibodies and the OB-fold domain (in particular the variant of a protein of the Sac7d family) retain their functionality, this indicates that they retain their structure. It is believed and hypothesized that the OB-fold domain, and in particular when selected as being a protein of the Sac7d family would stabilize the antibody chain during the production process and hence allow for an increase of yield. Consequently, the effect observed for the various complexes in the examples can be generalized with other antibodies and OB-fold variants that all possess the same structure.

SUMMARY OF THE INVENTION

The invention thus relates to a polypeptide that comprises a modified antibody. Said antibody is modified by the fusion of at least one variant of an OB-fold domain to at least one of the heavy or light chain of the immunoglobulin monomer, preferably at the N- or C-terminus of the light or heavy chain.

Said fusion is preferably made by genetic engineering, but chemical linkage of the OB-fold variant and of the heavy or light chain of the antibody is also foreseen.

Preferably, the variant comprises between 5 and 20 mutated residues in the binding site of the OB-fold domain to its natural ligand.

The OB-fold domain and the antibody may be able to bind different targets or different epitopes of the same target, thereby the protein herein disclosed would be able to bind to these multiple targets or to multiple epitopes of the given target.

As shown in FIG. 1 (which only illustrates symmetrical molecules), more than one variant of an OB-fold domain antibody may be bound to the light or heavy chain of the antibody. It is preferred when the protein of the invention is symmetrical (i.e. when it is composed of the same heterodimers), i.e. when the same OB-fold variant is fused to the two light or heavy chains of the protein. However, embodiments where only one OB-fold variant is bound to only one of the heavy or light chain are also included, as are embodiments where one OB-fold variant is bound to the light or the heavy chain of the protein, and another (different) OB-fold variant is bound to the other light or the heavy chain. Multiple combinations are thus possible, and FIG. 1 is not exhaustive.

In particular, as indicated OB-fold variants are fused to the two heavy or light chains of the antibody. The OB-fold variants can be identical or different on each of the heavy or light chain. In another embodiment, OB-fold variants are fused to at least one heavy chain and to at least one light chains of the antibody. The OB-fold variants may be identical or different on the heavy and light chains.

In another embodiment, two OB-fold variants (identical or different) are fused to the same light or heavy chain (at the N- and at the C-terminus of the chain).

The protein may contain one OB-fold variant. It may contain two OB-fold variants (it is preferred when these are identical and present symmetrically on the protein). It may contain three OB-fold variants. It may contain four OB-fold variants (it is preferred when there are two pairs of OB-fold variants and when the protein is symmetrical). It may contain five OB-fold variants. It may contain six OB-fold variants (it is preferred when there are three pairs of OB-fold variants and when the protein is symmetrical). It may contain seven OB-fold variants. It may contain eight OB-fold variants (it is preferred when there are four pairs of OB-fold variants; in this case, the protein would be symmetrical). It is reminded that a protein that is symmetrical is a protein that is made from identical heavy and light chains.

The invention also relates to a genetic construct comprising a DNA sequence selected from the group consisting of a. the sequence coding for the heavy chain of an antibody fused, at its 3' end with the sequence coding for a variant of an OB-fold protein
b. the sequence coding for the heavy chain of an antibody fused, at its 5' end with the sequence coding for a variant of an OB-fold protein
c. the sequence coding for the light chain of an antibody fused, at its 3' end with the sequence coding for a variant of an OB-fold protein
d. the sequence coding for the light chain of an antibody fused, at its 5' end with the sequence coding for a variant of an OB-fold protein These genetic sequences make it possible, when introduced in an appropriate host cell with the complementary antibody genetic sequence (the sequence coding for a light chain in case of a) or b), or the sequence coding for a heavy chain in case of c) or d)), to have production of the protein as herein disclosed. The invention also related to a vector comprising such genetic construct, as well as to a host cell (in particular an eukaryotic cell) comprising such genetic construct of claim in its genome (preferably with a complementary sequence).

The invention also relates to a method for producing the polypeptide of the invention, comprising the steps consisting of a. Culturing a cell culture wherein the cells have been transformed by a genetic construct as described and the complementary sequence for the antibody, and
b. recovering the polypeptide thus produced.

Such culture is made in conditions so as to express and have assembled the proteins expressed from the genetic construct. This method is particularly suitable when the polypeptide is secreted in the culture medium.

The invention also relates to method for producing the polypeptide of the invention, comprising the steps consisting of (a) culturing cells that have been transformed by a genetic construct as described and the complementary sequence for the antibody
(b) harvesting the cells; and
(c) disrupting the cells to obtain a crude extract containing the polypeptide as described.

Also comprised in the invention is a method for producing a genetic construct for production of the polypeptide as described, comprising the step of genetically fusing the sequence coding for a variant of an OB-fold domain to at least the 5' or 3' end of the heavy or the light chain of an antibody, and recovering the genetic construct thus obtained.

The invention also relates to a complex consisting of a polypeptide as herein disclosed, bound to at least one target through the OB-fold variant or the antibody binding site. Such target is thus the antigen of the antibody or the target to which the OB-fold variant binds.

The invention is particularly interesting as it makes it possible to obtain bi-specific or multi-specific molecules by a single and very easy method (an easy genetical modification consisting of the fusion of an antibody sequence (light or heavy chain coding sequence) to an OB-fold coding sequence.

In the preferred embodiments, the method makes it possible to make sure that 100% of the protein recovered after production in a cell transformed with appropriate genetic vectors are of the same type, thereby solving the problem of purification of bi-specific antibodies reminded above, where the statistical amount (and recovery) of the bispecific molecules are generally around 12.5% in the solution. Furthermore, the methods herein disclosed make it possible to obtain multi-specific molecules as diverse as can be the antibodies (chimeric, human, from mouse, rats, or from any idiotypes). it is also to be noted that, since the global structure of the antibody isn't modified, the molecules retain all the characteristics and properties of the antibodies (including any effect through the non-Fab's fragment, such as through the Fc fragments). It is also very surprising that the molecules herein disclosed are able to bind for both the antibody and OB-fold domain binding sites despite the modification made to the antibody. Such bi-specific binding ability thus suggests that proper folding of the polypeptide fragments molecules (antibody part and OB-fold domain part) is maintained. Finally, it was also surprising to note that production yield of the molecules is maintained (as compared to the antibody production yield), or even increased.

DETAILED DESCRIPTION OF THE INVENTION

The OB-Fold Domain

As indicated above, OB-fold domains can be engineered to variants that bind to specific targets, by introducing mutations within their binding site.

In the context of the present application, the term "OB-fold domain" (or "OB-fold protein") designates natural OB-fold proteins, but also the domains which have an OB-fold, and that can be isolated from more complex proteins. These OB-fold domains are in particular described in greater detail in WO 2007/139397 and WO 2008/068637. This term also comprises the polypeptides that can be obtained by fusing, by genetic engineering, in the N- or C-terminal position, an OB-fold protein or a domain which has an OB-fold to a protein or a domain of interest, for example a tag allowing better purification.

In the context of the present invention, it is however preferred to use only domains that have the OB-fold topology and not full proteins when such comprise other sequences that are not within the OB-fold domain. Indeed, it is preferred to use as small proteins as possible and preferably, the variant of the OB-fold domain, used in the context of the present invention, contains a maximum of 300 amino acids, preferably a maximum of 200 amino acids, preferably a maximum of 175 amino acids, more preferably a maximum of 150 amino acids, more preferably a maximum of 100 amino acids. In one particular embodiment, it contains a maximum of 80 or a maximum of 70 amino acids.

Binding Site of the OB-Fold Domain

The OB-fold proteins are known in the art. They are in particular described in the documents cited above, and also in Arcus (Curr Opin Struct Biol. 2002 December; 12(6): 794-801). OB-fold is in the form of a cylinder having five beta ($\beta$) sheets. Most OB-fold proteins use the same binding interface of their natural ligand, which may be an oligosaccharide, an oligonucleotide, a protein, a metal ion or a catalytic substrate. This binding interface comprises mainly the residues located in the beta sheets. Certain residues located in the loops may also be involved in the binding of an OB-fold protein with its natural ligand. Thus, applications WO 2007/139397 and WO 2008/068637 and the Arcus document (2002, op. cit.) describe the OB-fold-protein domains for binding with their natural ligand.

In particular, document WO 2008/068637 describes precisely how to identify the binding domain of an OB-fold protein.

By superimposing several sequences and 3D structures of proteins having OB-fold domains, using the websites WU-Blast2 (Lopez et al., 2003, Nucleic Acids Res 31, 3795-3798), T-COFFEE (Notredame et al., 2000, J Mol Biol 302, 205-217) and DALI lite (Holm and Park, 2000, Bioinformatics 16, 566-567), it is possible to identify the positions of the binding domains and in particular the amino acids which can be modified. Taking the sequence of Sac7d (SEQ ID NO: 1) as a reference, these are the residues V2, K3, K5, K7, Y8, K9, G10, E11, K13, E14, T17, K21, K22, W24, V26, G27, K28, M29, S31, T33, Y34, D36, N37, G38, K39, T40, R42, A44, S46, E47, K48, D49, A50 and P51.

The binding domains of other OB-fold proteins can be identified as described in WO 2008/068637. This application indicates that it is possible to perform a superimposition of 3D structures of OB-fold proteins or domains (10 domains were used in this application, including Sac7d), using the DALI website (Holm and Sander, 1998, Nucleic Acids Res 26, 316-319). Thus, it is easy to identify, for any OB-fold protein (or any OB-fold domain), the amino acids involved in the binding site and corresponding to the Sac7d amino acids mentioned above. Consequently, providing the amino acids that can be mutated in one of these proteins makes it possible to identify the corresponding amino acids for any other OB-fold domain.

It is also possible to delete some amino acids from the OB-fold scaffold. Still with this Sac7d sequence as reference, the residues which can be deleted are: A59, R60, A61, E62, R63, E64 and/or K66.

The teaching of WO 2008/068637 also indicates that amino acids can optionally be inserted into the loops of the OB-fold proteins, in particular the proteins of the Sac7d family; in particular, insertions of 1 to 15 amino acid residues can be made in loop 3 (as defined in FIGS. 1b and 2 of WO 2008/068637), for example in the region of residues 25 to 30 of Sac7d, preferably between residues 27 and 28, insertions of 1 to 15 amino acid residues can be made in loop 4 (as defined in FIGS. 1b and 2 of WO 2008/068637), for example in the region of residues 35-40 of Sac7d, preferably between residues 37 and 38, and insertions of 1 to 20 residues can be made in loop 1 (as defined in FIGS. 1b and 2 of WO 2008/068637), for example in the region of residues 7 to 12 of Sac7d, preferably between residues 9 and 10.

Obtaining Mutants of an OB-Fold Domain

WO 2007/139397 describes the use of libraries of OB-fold proteins in which the OB domain is modified by introducing mutations into this domain for binding of the protein to its natural ligand. In particular and as foreseen herein, modified OB-fold domain comprises a) at least one modified amino acid residue in a β-strand of the OB-fold domain binding face as compared to the naturally occurring OB-fold domain, or b) at least one modified amino acid residue in a β-strand of the OB-fold domain binding face and at least one modified amino acid residue in a strand of the OB-fold domain loop region, or c) at least one modified amino acid residue in a strand of the OB-fold domain loop region. Generally, the modified OB-fold domain has altered binding characteristics as compared to the naturally occurring OB-fold domain.

WO 2008/068637 describes the use of a library based on the Sac7d protein for obtaining ligands which have an affinity for targets of interest. The method described in WO 2008/068637 comprises the generation of combinatorial libraries containing a plurality of DNA molecules all having the same sequence, except for the presence of certain random mutations leading to the production of variants of a wild-type protein, exhibiting mutations at certain amino acids of the binding site of this wild-type OB-fold protein. In particular, in the context of WO 2008/068637, the wild-type OB-fold protein is a Sac7d protein, into which mutations are introduced in order to generate a variability, in particular at amino acids chosen from K7, Y8, K9, K21, K22, W24, V26, M29, S31, T33, T40, R42, A44, S46, or on other amino acids, such as V26, G27, K28, M29, S31, R42, A44, S46, E47 and K48. These amino acids are based on the Sac7d sequence, as represented by SEQ ID NO: 1.

WO 2012/150314 shows that the mutations from one protein of the Sac7d family can be carried to another protein of the same family. This portability amounts to creating a mutant of another protein of the Sac7d family, starting from a mutant of one protein of said family. The first mutant may have been obtained in particular by carrying out the process of WO 2008/068637.

It has already been shown that it is possible to obtain such mutants against a given target (and especially when the target is a protein or a peptide). One can cite variants binding to immunoglobulins (Behar et al, Protein Engineering, Design & Selection vol. 26 no. 4 pp. 267-275, 2013), or to other proteins (WO WO 2008/068637). Gera et al (J Mol Biol. 2011 Jun. 17; 409(4):601-16) have also shown the possibility to obtain such proteins starting from Sso7d. Gocha et al (Scientific Reports 7, Article number: 12021 (2017)) also reported ability to obtain mutants from Sso7d.

Examples of OB-Fold Domains

Non-limitative examples of OB-fold proteins which can be used according to the invention are Sac7d, Sso7d, the N-terminal domain of SEB (Papageorgiou et al., 1998), the chain A of the Shiga-like toxin Ile (PDB 2bosa), the human Neutrophil Activatin Peptide-2 (NAP-2, PDB 1tvxA), the Molybdenum Binding Protein (modg) of *Azotobacter vinelandii* (PDB 1h9j), the N-terminal domain of SPE-C (Roussel et al., 1997), the B5 subunit of *E. coli* Shiga-like toxin (Kitov et al., 2000), Cdc13 (Mitton-Fry et al., 2002), the cold-shock DNA-binding domain of the human Y-box protein YB-1 (Kloks et al., 2002), the *E. coli* inorganic pyrophosphatase EPPase (Samygina et al., 2001), or any of the proteins listed in Table 3 of the article by (Arcus, 2002), such as 1krs (Lysyl-tRNA synthetase LysS, *E. coli*), 1c0aA (Asp-tRNA synthetase, *E. coli*), 1b8aA (Asp-tRNA synthetase, *P. kodakaraensis*), 1lyIA (Lysyl-tRNA synthetase LysU, *E. coli*), 1quqA (Replication protein A, 32 kDa subunit, Human), 1quqB (Replication protein A, 14 kDa subunit, Human), 1jmcA (Replication protein A, 70 kDa subunit (RPA70) fragment, Human), 1otc (Telomere-end-binding protein, *O. nova*), 3ullA (Mitochondrial ssDNA-binding protein, Human), 1prtF (Pertussis toxin S5 subunit, *B. pertussis*), 1bcpD (Pertussis toxin S5 subunit (ATP bound), *B. pertussis*), 3chbD (Cholera Toxin, *V. cholerae*), 1tiiD (Heat-labile toxin, *E. coli*), 2bosA (Verotoxin-1/Shiga toxin, B-pentamer, *E. coli*), 1br9 (TIMP-2, Human), 1an8 (Superantigen SPE-C, *S. pyogenes*), 3seb (Superantigen SPE, *S. aureus*), 1aw7A (Toxic shock syndrome toxin, *S. aureus*), 1jmc (Major cold-shock protein, *E. coli*), 1bkb (Initiation translation factor 5a, *P. aerophylum*), 1sro (S1 RNA-binding domain of PNPase, *E. coli*), 1d7qA (Initiation translation factor 1, elF1a, Human), 1ah9 (Initiation translation factor 1, IF1, *E. coli*), 1b9 mA (Mo-dependent transcriptional regulator ModE, *E. coli*), 1ckmA (RNA guanyl-yltransferase, *Chlorella* virus, PBCV-1), 1a0i (ATP-dependent DNA ligase, Bacteriophage T7), 1snc (Staphylococcal nuclease, *S. aureus*), 1 hjp (DNA helicase RuvA subunit, N-terminal domain, *E. coli*), 1pfsA (Gene V protein, *Pseudomonas* bacteriophage pf3), 1gvp (Gene V protein, Filamentous bacteriophage (f1, M13)), 1gpc (Gene 32 protein (gp32) core, Bacteriophage T4), 1wgjA (Inorganic pyrophosphatase, *S. cerevisiae*), and 2prd (Inorganic pyrophosphatase, *T. thermophilus*).

A Specific and Preferred Example of an OB-Fold Domain

The Sac7d family is defined as relating to the Sac7d protein and corresponds to a family of 7 kDa DNA-binding proteins isolated from extremophilic bacteria.

These proteins and this family are in particular described in WO 2008/068637. Thus, within the context of the present invention, a protein belongs to the Sac7d family when it has one of the sequences SEQ ID NO: 1 to SEQ ID NO: 14, or when it has a sequence corresponding to the sequence SEQ ID NO: 15, which is a consensus sequence (obtained from SEQ ID NO: 1 to SEQ ID NO: 9 and SEQ ID NO: 12 to SEQ ID NO: 14. In this consensus sequence, a dash — indicates no amino acid, the proteins not having all the same size). This Sac7d family comprises in particular the Sac7d or Sac7e proteins derived from *Sulfolobus acidocaldarius*, the Sso7d protein derived from *Sulfolobus solfataricus*, the DBP 7 also called Sto7 protein derived from *Sulfolobus tokodaii*, the Ssh7b protein derived from *Sulfolobus shibatae*, the Ssh7a protein derived from *Sulfolobus shibatae*, Mse7 derived from *Metallosphaera sedula*, Mcu7 derived from *Metallosphaera cuprina*, Aho7a or Aho7b or Aho7c derived from Acidianus hospitalis, Sis7a or Sis7b derived from *Sulfolobus islandicus* and the p7ss protein derived from *Sulfolobus solfataricus*. In view of the broad similarity of the sequences of the proteins of the Sac7d family, it is directly possible and easy to identify the amino acids of another protein than Sac7d that correspond to given amino acids of Sac7d.

It is to be noted that the number of mutated residues in said variant (relative to the wild-type protein) is preferably between 5 and 25. The invention can be implemented with variants preferably having at least 5, more preferably at least 7 or 8, even more preferably at least 10, but generally less than 25, more preferably less than 24, even more preferably less than 20 or less than 15 or 14 substituted amino acids compared with the wild-type OB-fold protein (or domain). It is preferred when 7, 8, 9, 10, 11, 12, 13 or 14 amino acids are mutated in the binding site of the OB-fold domain, relative to the wild-type OB-fold domain. These mutations are introduced in the amino acids corresponding to V2, K3, K5, K7, Y8, K9, G10, E11, K13, E14, T17, K21, K22, W24, V26, G27, K28, M29, S31, T33, Y34, D36, N37, G38, K39, T40, R42, A44, S46, E47, K48, D49, A50 and P51 of Sac7d (SEQ ID NO: 1)

In a particular embodiment, the number of mutated amino acids is between 7 and 14 (limits included).

In one particular embodiment, these variants can also comprise amino acid insertions as indicated above.

As indicated, proteins of the Sac7d family are Sac7d or Sac7e derived from *Sulfolobus acidocaldarius*, Sso7d derived from *Sulfolobus solfataricus*, DBP 7 also called Sto7 derived from *Sulfolobus tokodaii*, Ssh7b derived from *Sulfolobus shibatae*, Ssh7a derived from *Sulfolobus shibatae*, Mse7 derived from *Metallosphaera sedula*, Mcu7 derived from *Metallosphaera cuprina*, Aho7a or Aho7b or Aho7c derived from *Acidianus hospitalis*, Sis7a or Sis7b derived from *Sulfolobus islandicus* and p7ss derived from *Sulfolobus solfataricus*. The various sequences of the Sac7d, Sso7d, Sac7e, Ssh7b, Ssh7a, DBP7, Sis7a (3 alleles), Mse7, Mcu7, Aho7a, Aho7b and Aho7c proteins are represented by SEQ ID NO: 1 to SEQ ID NO: 14 respectively.

A variant of a protein of this Sac7d family may be called a nanofitin. The invention is thus preferentially implemented on variants of the proteins represented by any of SEQ ID NO: 1 to SEQ ID NO: 14, or a protein having the sequence SEQ ID NO: 15, in particular on variants of Sac7d.

In a preferred embodiment, the mutated amino acids are selected in the group consisting of V2, K3, K5, K7, Y8, K9, G10, E11, K13, E14, T17, K21, K22, W24, V26, G27, K28, M29, S31, T33, Y34, D36, N37, G38, K39, T40, R42, A44, S46, E47, K48, D49, A50 and P51 (reference is made to SEQ ID NO: 1, and to the alignment of FIG. 2). From the alignment of FIG. 2, it is possible to identify the amino acids corresponding to the above-identified amino acids of Sac7d, in any other protein. It is to be noted that the variant shall comprise mutated amino-acids (preferably from 7 to 12 as indicated above) chosen among these amino acids, and may also contain other mutated amino acids (preferably from 0 to 5) in other regions (i.e. chosen among other residues of Sa7d). As indicated above, A59, R60, A61, E62, R63, E64 and/or K66 can be deleted.

In a preferred embodiment, the mutated amino acids are selected from the group consisting of K7, Y8, K9, K21, K22, W24, V26, M29, S31, T33, T40, R42, A44, and S46.

The variants herein disclosed can be obtained by the method described in WO 2008/068637 (various rounds of enrichment of the combinatorial libraries, in particular using ribosome display).

The variant of OB-fold domain is thus preferably a variant of a protein of the Sac7d family (Sac7d variant), comprising from 5 to 20 (preferably from 7 to 14) mutated amino acids in the binding site of the protein. Preferably, the mutated amino acids of the Sac7d variant are selected from the group consisting of V2, K3, K5, K7, Y8, K9, G10, E11, K13, E14, T17, K21, K22, W24, V26, G27, K28, M29, S31, T33, Y34, D36, N37, G38, K39, T40, R42, A44, S46, E47, K48, D49, A50 and P51 (in reference to SEQ ID NO:1 and the alignment of FIG. 2). Preferably the Sac7d variant contains 7 to 14 mutated amino acids chosen in the group consisting of K7, Y8, K9, K21, K22, W24, V26, M29, S31, T33, T40, R42, A44, and S46.

The advantage of the method described in WO 2008/068637 is that it makes it possible to obtain variants of OB-fold proteins by screening combinatorial libraries containing or expressing a plurality of variants in which a certain number of amino acids have been "randomized", i.e. replaced with a random amino acid. The screening of these libraries makes it possible to identify variants of these proteins which bind specifically, generally with a strong affinity (application WO 2008/068637 in fact describes affinities of the order of one nanomolar), with a target of interest, other than the natural ligand of the wild-type protein from which the combinatorial library was generated.

As indicated above, the applicant was able to show that it is possible to make specific binding proteins by fusing a OB-fold domain binding to a given target to a heavy chain or a light chain of an antibody that binds either to the same target (thereby increasing specificity and affinity) or to another target (thereby obtaining a multi-specific binding protein).

This fusion can be made at the N-terminus and/or the C-terminus of the antibody chain (heavy and/or light chain). It is to be noted that, especially when using a small OB-fold domain (about 70 amino acids) such as a protein from the Sac7d family, it is possible to obtain a molecule that will have the structure of the antibody (two light chains paired to two heavy chains, and such dimers paired together), with the antibody regions, and further binding regions consisting of the modified OB-fold domain.

Antibodies

Antibodies are large, Y-shaped proteins that recognize an antigen, via the Fab's variable region. They are typically made of four polypeptide chains; two identical heavy chains (of about 400 to 500 amino acids) and two identical light chains (of about 211 to 217 amino acids) connected by disulfide bonds. Each chain is composed of structural domains called immunoglobulin domains.

There are several different types of antibody heavy chains that define the five different types of fragments (Fc) that may be attached to the antigen-binding fragments, and which allow antibodies to be grouped into five isotypes (IgA, IgD, IgE, IgG, and IgM). Each heavy chain has a constant region and a variable region, the constant region being identical in all antibodies of the same isotype, but differing in antibodies of different isotypes.

In a specific embodiment, the antibody part of the protein herein disclosed is a IgG molecule.

In another embodiment, the antibody part of the protein herein disclosed is a IgA molecule.

In another embodiment, the antibody part of the protein herein disclosed is a IgM molecule.

In another embodiment, the antibody part of the protein herein disclosed is a IgD molecule.

In another embodiment, the antibody part of the protein herein disclosed is a IgE molecule.

The antibody may be a human antibody, a rodent antibody (such as a mouse antibody or a rat antibody), a cat antibody, a dog antibody, a chicken antibody, a goat antibody, a camelid antibody (such as a camel antibody, a llama antibody, an alpaca antibody or a nanobody), a shark antibody, or an antibody from any other species. It may be a chimeric or humanized antibody. As reminded in Wikipedia, humanized antibodies are antibodies from non-human species whose protein sequences have been modified to increase their similarity to antibody variants produced naturally in humans. A chimeric antibody contains sequences from different species.

It is preferred when the antibody that is part of the molecule herein disclosed is an antibody that comprises two identical heavy chains (of about 400 to 500 amino acids, generally around 450 amino acids) and two identical light chains. Consequently, the antibody comprises the same Fab variable regions. This antibody is therefore a monospecific antibody where both parts (combination of light and heavy chains) of the antibody bind to the same epitope of an antigen.

However, the antibody may present different heavy and/or light chains. In particular, in some embodiments, the antibody is a bi-specific antibody. The term "antibody" thus encompasses both "classical antibodies" as disclosed above having identical heavy and light chains, but also engineered antibodies that have more than one specificity.

In a specific embodiment, the antibody presents one heavy and light chain from one antibody and another heavy and light chain from another antibody.

In particular, the antibody usable in the molecules herein disclosed may be a triomab (Trion Pharma), a KIH (knobs-into-holes) IgG (Xu et al, MAbs. 2015; 7(1): 231-242, Dillon et al, MABS 2017, 9 (2), 213-230) (possibly with a common Light Chain, as shown in Klein et al MAbs. 2012 Nov. 1; 4(6): 653-663), a cross-Mab (Roche Technology, Klein et al, MAbs. 2016 August-September; 8(6): 1010-1020, Cain, Chris. (2011). Crossing over to bispecificity. Science-Business eXchange.), an ortho-Fab IgG (Lewis et al, Nat Biotechnol. 2014; 32(2):191-8), a DVD (dual-variable-domain) IgG (developed by AbbVie), a 2 in1-IgG (developed by Genetech), an IgG-scFv (Orcutt er al, Protein Eng Des Sel. 2010 April; 23(4):221-8) or a DNL-Fab3. All these antibodies are disclosed in FIG. 2 of Kontermann and Brinkmann (Drug Discovery Today, 20 (7), 2015, 838-847) or in Brinkmann and Kontermann (MABS, 2017, 9 (2), 182-212). Fan et al (Journal of Hematology & Oncology (2015) 8:130) also describes bispecific antibodies and their applications.

The Triomab® family of trifunctional, bispecific antibodies that maintain an IgG-like shape are chimeras that consist of two half antibodies, each with one light and one heavy chain, that originate from parental mouse IgG2a and rat IgG2b isotypes.

In a specific embodiment, the antibody is a therapeutic antibody. Such therapeutic antibodies can be used in humans to cure diseases, delay evolution of diseases or alleviate symptoms of diseases.

The therapeutic antibody is preferably selected from the group consisting of:

3F8, 8H9, Abagovomab, Abciximab, Abituzumab, Abrilumab, Actoxumab, Adalimumab, Adecatumumab, Aducanumab, Afasevikumab, Afelimomab, Afutuzumab, Alacizumab pegol, ALD518, Alemtuzumab, Alirocumab, Altumomab pentetate, Amatuximab, Anatumomab mafenatox, Anetumab ravtansine, Anifrolumab, Anrukinzumab, Apolizumab, Arcitumomab, Ascrinvacumab, Aselizumab, Atezolizumab, Atinumab, Atorolimumab, Avelumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cergutuzumab amunaleukin, Certolizumab pegol, Cetuximab, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Crotedumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dinutuximab, Diridavumab, Domagrozumab, Dorlimomab aritox Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, Epratuzumab, Erenumab, Erlizumab, Ertumaxomab, Etaracizumab, Etrolizumab, Evinacumab, Evolocumab, Exbivirumab, Fanolesomab, Faralimomab, Farletuzumab, Fasinumab, FBTA05, Felvizumab, Fezakinumab, Fibatuzumab, Ficlatuzumab, Figitumumab, Firivumab, Flanvotumab, Fletikumab, Fontolizumab, Foralumab, Foravirumab, Fresolimumab, Fulranumab, Futuximab, Galcanezumab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, Igovomab, IMAB362, Imalumab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Ipilimumab, Iratumumab, Isatuximab, Itolizumab, Ixekizumab, Keliximab, Labetuzumab, Lampalizumab, Lanadelumab, Landogrozumab, Laprituximab emtansine, Lebrikizumab, Lemalesomab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, MABp1, Mapatumumab, Margetuximab, Maslimomab, Matuzumab, Mavrilimumab, Mepolizumab, Metelimumab, Milatuzumab, Minretumomab, Mirvetuximab soravtansine, Mitumomab, Mogamulizumab, Monalizumab, Morolimumab, Motavizumab, Moxetumomab pasudotox, Muromonab-CD, Nacolomab tafenatox, Namilumab, Naptumomab estafenatox, Naratuximab emtansine, Narnatumab, Natalizumab, Navicixizumab, Navivumab, Nebacumab, Necitumumab, Nemolizumab, Nerelimomab, Nesvacumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Risankizumab, Rituximab, Rivabazumab pegol, Robatumumab, Roledumab, Romosozumab, Rontalizumab, Rovalpituzumab tesirine, Rovelizumab, Ruplizumab, Sacituzumab govitecan, Samalizumab, Sapelizumab, Sarilumab, Satumomab pendetide, Secukinumab, Seribantumab, Setoxaximab, Sevirumab, SGN-CD19A, SGN-CD33A, Sibrotuzumab, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tamtuvetmab, Tanezumab, Taplitumomab paptox, Tarextumab, Tefibazumab, Telimomab aritox, Tenatumomab, Teneliximab, Teplizumab, Teprotumumab, Tesidolumab, Tetulomab, Tezepelumab, TGN1412, Ticilimumab (=tremelimumab), Tigatuzumab, Tildrakizumab, Timolumab, Tisotumab vedotin, TNX-650, Tocilizumab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Vobarilizumab, Volociximab, Vorsetuzumab mafodotin, Votumumab, Xentuzumab, Zalutumumab, Zanolimumab, Zatuximab, Ziralimumab, and Zolimomab aritox.

In particular, such therapeutic antibody is selected from the group consisting of Adalimumab (against TNFa, sold under the name of Humira®); Infliximab (against TNFa, sold under the name of Remicade®); Cetuximab (against EGFR sold as Erbitux®); Secukinumab (against IL17 sold as Cosentyx®); Pembrolizumab (against PD1 sold as Keytruda®); Bevacizumab (against VEGF-A sold as Avastin®); Etrolizumab (against a4b7); vedolizumab (against a4b7); Tremelimumab (against CTLA4); Ipilimumab (against CTLA4 sold as Yervoy®); Necitumumab (against EGFR sold as Portrazza®); Panitumumab (against EGFR, sold as Vectibix®); Lebrikizumab (against IL13); Tralokinumab (against IL13); Ixekizumab (against IL17, sold as Taltz®); Brodalumab (against IL17R, sold as Lumicef®); Dupilumab (against IL4R, sold as Dupixent®); Guselkumab (against IL23); Tildrakizumab (against IL23); Risankizumab (against IL23); Briakinumab (against IL12 and IL23); Ustekinumab (against IL12 and IL23); Nivolumab (against PD1, sold as Opdivo®); Atezolizumab (against PD-L1, sold as Tecentriq®); Avelumab (against PD-L1); Ranibizumab (against VEGF-A sold as, Lucentis®); Brolucizumab (against VEGF-A); Trastuzumab (against Her2, Herceptin®); Amatuximab (against Mesothelin); Tavolixizumab (against OX40); Pogalizumab (against OX40); Urelumab (against 4-1BB); Utomilumab (against 4-1BB); BMS 986016 (against LAG3); lirilumab (against KIR); MEDI 570 (against ICOS); LY3321367 (against TIM3); lulizumab (against CD28); TAB08 (against CD28); and Onartuzumab (against cMet, MetMab).

Targets

Targets of the multi-specific molecule of the invention can be any molecule or antigen of interest. in particular, the multi-specific molecule is targeted to a cancer or hyperproliferative disease, for example, lymphoma (e.g., non-Hodgkin's lymphoma), renal cell carcinoma, prostate cancer, ovarian cancer, breast cancer, colorectal cancer, neuroendodrine cancer, endometrial cancer, pancreatic cancer leukemia, lung cancer, glioblastoma multiforme, stomach cancer, liver cancer, sarcoma, bladder cancer, testicular cancer, esophageal cancer, head and neck cancer, and leptomeningeal carcinomatosis.

In a preferred embodiment, the OB-fold domain binds to a target as disclosed below.

It may be selected from the group consisting of:
Cell surface receptors: Insulin receptor, Low density lipoprotein receptor-related protein 1, Transferrin receptor, Epidermal growth factor receptor, Epidermal growth factor receptor variant III, Vascular endothelial growth factor receptor 1, Vascular endothelial growth factor receptor 2, Her2, Her3, Her4, PMSA, IGF-1R, GITR, RAGE, CD28.
Cell surface proteins: Mesothelin, EpCam, CD19, CD20, CD38, CD3, TIM-3, CEA, cMet, ICAM1, ICAM3, MadCam, a4b7, CD7, CD4, CD138.
Angiogenesis or Growth factors: VEGF, Angiopoietin 2, HGF, PDGF, EGF, GM-CSF, HB-EGF, TGF
Immune checkpoint inhibitors or activators: PD-1, PD-L1, CTLA4, CD28, B7-1, B7-2, ICOS, ICOSL, B7-H3, B7-H4, LAG3, KIR, 4-1BB, OX40, CD27, CD40L, TIM3, A2aR
Circulating protein: TNFa, IL23, IL12, IL33, IL4, IL13, IL5, ILO, IL4, IFNg, IL17, RANKL, Bace1, alpha Synuclein, Tau, amyloid.

In a preferred embodiment, the antibody part of the molecule binds to a target selected in the group consisting of:
Cell surface receptors: Insulin receptor, Low density lipoprotein receptor-related protein 1, Transferrin receptor, Epidermal growth factor receptor, Epidermal growth factor receptor variant III, Vascular endothelial growth factor receptor 1, Vascular endothelial growth factor receptor 2, Her2, Her3, Her4, PMSA, IGF-1R, GITR, RAGE, CD28.
Cell surface proteins: Mesothelin, EpCam, CD19, CD20, CD38, CD3, TIM-3, CEA, cMet, ICAM1, ICAM3, MadCam, a4b7, CD7, CD4, CD138.
Angiogenesis factors and Growth factors: VEGF, Angiopoietin 2, HGF, PDGF, EGF, GM-CSF, HB-EGF, TGF
Immune checkpoint inhibitors or activators: PD-1, PD-L1, CTLA4, CD28, B7-1, B7-2, ICOS, ICOSL, B7-H3, B7-H4, LAG3, KIR, 4-1BB, OX40, CD27, CD40L, TIM3, A2aR
Circulating proteins: TNFa, IL23, IL12, IL33, IL4, IL13, IL5, ILO, IL4, IFNg, IL17, RANKL, Bace1, alpha Synuclein, Tau, amyloid.

In a preferred embodiment, the molecule binds to the following couples of targets (one of such listed targets may be of the OB-fold domain, whereas the other may be of the antibody part).
EGFR/EGFRvIII
EGFR/Her2
VEGFR2/PD1

EGFR/PD1
VEGF/PD-L1
PD1/OX40
PD1/CTLA4
EGFR/CD3
TNFa/IL17
IL13/IL4

Complexes where the antibody binds to TNFalpha and the OB-fold domain binds to IL17, and vice versa, are particularly interesting and preferred.

Further examples of couples of targets are disclosed below. It is to be noted that the antibody part of the molecule may bind to any one of the listed targets and the OB-fold variant bind to the other target. Consequently, any of the above listed targets are valid for either the antibody part or the OB-fold variant part of the molecule.

Production of the Artificial Molecules

The vectors allowing the production of the molecules herein disclosed are manufactured by regular molecular genetic methods.

In summary, the genetic sequence coding for the Sca7d variant is ligated to the 5' or the 3' end of the genetic sequence coding for the heavy or the light chain of the antibody, by any method known in the art. It is possible to introduce a linker between the two genetic sequences, as long as no frame shift or stop codon is introduced, so as to obtain a fusion protein.

The expressed fusion protein shall thus be either (from N-terminus to C-terminus):

(a) heavy chain of antibody—(linker if present)—OB-fold domain variant
(b) OB-fold domain variant—(linker if present)—heavy chain of antibody
(c) light chain of antibody—(linker if present)—OB-fold domain variant
(d) OB-fold domain variant—(linker if present)—light chain of antibody It is clear that further genetic modifications can be foreseen such as further introduction of "tag" molecules at the C or N-terminus so as to improve purification, or to compel the orientation of the OB-fold, or to allow a protease mediated release of the OB-fold, or to modify the pharmacokinetics of the compound, or to target a specific type of tissue, or to chelate lanthanide or radionucleide, or to allow conjugation to a payload that can be a maytansine or an auristatin derivative.

It is to be noted that the codon of the genetic sequences can be optimized (see for instance the OptimumGene™ codon optimization technology of GenSript, Piscataway, NJ USA) for further production, depending on the cell that is used for such production.

As indicated below, other nucleic acid molecules can be obtained such as nucleic acid molecules coding for:

(a) OB fold domain variant—(linker if present)—heavy chain of antibody—(linker if present)—OB fold domain variant
(b) OB fold domain variant—(linker if present)—light chain of antibody —(linker is present)—OB fold domain variant These recombinant DNA constructs comprising one or more of the nucleotide sequences described above are used in connection with a vector, such as a plasmid, phagemid, phage or viral vector.

These recombinant acid molecules can be produced by techniques described in Sambrook et al., 1989 (Sambrook J, Fritschi E F and Maniatis T (1989) Molecular cloning: a laboratorymanual, Cold Spring Harbor Laboratory Press, New York). Alternatively, the DNA sequences may be chemically synthesized using, for example, synthesizers.

Recombinant constructs of the invention comprise the expression vectors that are capable of expressing the RNA and thus lead to production of proteins from the above genetic sequences. The vector may thus further comprise regulatory sequences, including a suitable promoter operably linked to the open reading frame (ORF) of the genetic sequences herein disclosed. The vector may further comprise a selectable marker sequence such as an antibiotic resistance gene. Specific initiation and bacterial secretory signals also may be required for efficient translation of the coding sequences when bacteria as used as the expression host.

Production of the Molecules

Cells are transfected or transformed with vectors containing sequences coding for the heavy and light chain of the antibody. At least one of the sequences includes the variant of the OB-fold protein, as discussed above.

The cells are the cultured in such conditions as to have the protein expressed and favorably secreted. The conditions of culture of the cells are the conditions generally used for recombinant antibody production and are known in the art. Such conditions that are known in the art can also be optimized by the person skilled in the art if needed. Kunert and Reinhart (Appl Microbiol Biotechnol. 2016; 100: 3451-3461) review such methods and provide ample references thereto.

One can use bacterial, phage (Shukra et al, Eur J Microbiol Immunol (Bp). 2014; 4(2): 91-98) or eukaryotic systems of production.

One shall prefer to use eukaryotic cells in order to obtain proper post-translational modifications such as glycosylation.

In particular, one can use CHO (Chinese Hamster Ovary) cells, PER.C6 cells (human cell line, Pau et al, Vaccine. 2001 21; 19(17-19):2716-21), HEK 293b cells (Human embryonic kidney cells 293), NS0 cells (cell line derived from the non-secreting murine myeloma) or EB66 cells (a duck cell line Valneva, Lyons, France).

Also provided by the present disclosure are host cells containing at least one of the DNAs constructs described above. The host cell can be any cell for which expression vectors are available. As indicated above, it may be a higher eukaryotic host cell, such as a mammalian cell, a lower eukaryotic host cell, such as a yeast cell, or a prokaryotic cell, such as a bacterial cell.

Introduction of the recombinant construct into the host cell is performed by any method known in the art (such as calcium phosphate transfection, lipofection, DEAE, dextran mediated transfection, electroporation or phage infection). The vectors can be inserted within the genome of the host cell, or be maintained as an extragenomic vector (such as a Bacterial Artificial Chromosome or a Yeast Artificial Chromosome). When introduced within the cell genome, such introduction may be random or targeted using methods known in the art (homologous recombination or the like).

Bacterial Hosts and Expression

Useful expression vectors for bacterial use are constructed by inserting the recombinant DNA sequence together with suitable translation initiation and termination signals in operable reading phase with a functional promoter. The vector will comprise one or more phenotypic selectable markers and an origin of replication to ensure maintenance of the vector and, if desirable, to provide amplification within the host.

Suitable prokaryotic hosts for transformation include *E. coli, Bacillus subtilis, Salmonella typhimurium* and various species within the genera *Pseudomonas, Streptomyces*, and *Staphylococcus*.

Eukaryotic Hosts and Expression

Examples of the eucaryotic host cells include vertebrate cells, insect cells, and yeast cells. In particular, one can use the cells mentioned above.

The transformed or transfected cells are cultured according to methods known in the art and the polypeptide are recovered from intracellular or extracellular fractions (depending on whether it is secreted or not).

Isolation of the Molecules

The recombinant multi-specific protein produced can be separated and purified by any of various known separation methods utilizing the physical or chemical property of the protein, from the intracellular or extracellular fraction.

In particular, one can use methods such as precipitation, ultrafiltration, various types of liquid chromatography such as molecular sieve chromatography (gel filtration), adsorption chromatography, ion exchange chromatography, and affinity chromatography, dialysis, and a combination thereof.

In general, any method known and used to purify recombinant antibodies is adapted for the purification of the molecules herein disclosed.

If a tag has been introduced within the recombinant sequence (such as a poly-Histidine tag), one can purify the molecules using this tag. However, it is preferred to use affinity to purify the molecules.

If the antibodies part of the molecule are of the IgG type, one can use affinity-chromatography with Protein A (see in particular Fahrner et al Biotechnol Appl Biochem. 1999 October; 30 (Pt 2):121-8).

Alternatively, one can use the methods disclosed in Jiang et al (Protein Expression and Purification, Volume 76, Issue 1, March 2011, Pages 7-14) that disclosed a purification process of a recombinant monoclonal antibody expressed in glycoengineered *Pichia pastoris*)

One can also use the method of Maria et al (J Chromatogr A. 2015 May 8; 1393:57-64) relating to a purification process of recombinant monoclonal antibodies with mixed mode chromatography or of Liu et al (MAbs. 2010 September-October; 2(5): 480-499) pertaining to the recovery and purification process for monoclonal antibody production.

One can, in particular, use the fact that the molecule herein produced binds to specific targets (antigen of the antibody and target of the OB-fold variant) and use any affinity method (affinity column, FACS, beads) to isolate such molecules.

One particular advantage of the method of the invention is that all resulting molecule that is produced by the cells are multi-specific molecules.

Production of Bi-Specific Molecules

In particular, one shall introduce, within the cell:

- A genetic sequence coding for a light chain of an antibody
- A genetic sequence coding for the heavy chain of the antibody, with the introduced variant of the OB-fold domain at the 5' end of such heavy chain.

The resulting molecule will be, after association of the heavy and light chains, a bi-specific molecule, binding to the antigen of the antibody and to the target of the variant of the OB-fold domain, said variant of the OB-fold domain being at the N-terminus of the heavy chains.

It is to be noted that the resulting molecules are symmetrical and shall have four binding sites (the two antibody Fab binding sites, and the binding sites of the two variants of the OB-fold domain at the N-terminus of the heavy chains), as depicted in FIG. 1.A.

In another embodiment, one shall introduce, within the cell:

- A genetic sequence coding for a light chain of an antibody
- A genetic sequence coding for the heavy chain of the antibody, with the introduced variant of the OB-fold domain at the 3' end of such heavy chain.

The resulting molecule will be, after association of the heavy and light chains, a bi-specific molecule, binding to the antigen of the antibody and to the target of the variant of the OB-fold domain, said variant of the OB-fold domain being at the C-terminus of the heavy chains.

It is to be noted that the resulting molecules are symmetrical and shall have four binding sites (the two antibody Fab binding sites, and the binding sites of the two variants of the OB-fold domain at the C-terminus of the heavy chains), as depicted in FIG. 1.B.

In another embodiment, one shall introduce, within the cell:

- A genetic sequence coding for a light chain of an antibody, with the introduced variant of the OB-fold domain at the 5' end of such light chain.
- A genetic sequence coding for the heavy chain of the antibody The resulting molecule will be, after association of the heavy and light chains, a bi-specific molecule, binding to the antigen of the antibody and to the target of the variant of the OB-fold domain, said variant of the OB-fold domain being at the N-terminus of the light chains.

It is to be noted that the resulting molecules are symmetrical and shall have four binding sites (the two antibody Fab binding sites, and the binding sites of the two variants of the OB-fold domain at the N-terminus of the light chains), as depicted in FIG. 1.C.

In another embodiment, one shall introduce, within the cell:

- A genetic sequence coding for a light chain of an antibody, with the introduced variant of the OB-fold domain at the 3' end of such light chain.
- A genetic sequence coding for the heavy chain of the antibody The resulting molecule will be, after association of the heavy and light chains, a bi-specific molecule, binding to the antigen of the antibody and to the target of the variant of the OB-fold domain, said variant of the OB-fold domain being at the C-terminus of the light chains.

It is to be noted that the resulting molecules are symmetrical and shall have four binding sites (the two antibody Fab binding sites, and the binding sites of the two variants of the OB-fold domain at the C-terminus of the light chains), as depicted in FIG. 1.D.

In another embodiment, one shall introduce, within the cell:

- A genetic sequence coding for a light chain of an antibody, with the introduced variant of the OB-fold domain at the 3' end of such light chain.
- A genetic sequence coding for the heavy chain of the antibody
- A genetic sequence coding for the light chain of the antibody The resulting products will be, after association of the heavy and light chains,

- a symmetrical bi-specific molecule, binding to the antigen of the antibody and to the target of the variant of the OB-fold domain, said variant of the OB-fold domain being at the C-terminus of the light chains (expected percentage 25%).

a non-symmetrical bi-specific molecule, binding to the antigen of the antibody and to the target of the variant of the OB-fold domain, said variant of the OB-fold domain being at the C-terminus of only one of the light chain (expected percentage 50%).

the symmetrical antibody (expected percentage 25%).

It is to be noted that the resulting molecules are symmetrical and shall have four binding sites (the two antibody Fab binding sites, and the binding sites of the two variants of the OB-fold domain at the C-terminus of the light chains).

Other combinations can be performed when transforming the cells with:

A genetic sequence coding for a light chain of an antibody, with the introduced variant of the OB-fold domain at the 5' end of such light chain.

A genetic sequence coding for the heavy chain of the antibody A genetic sequence coding for the light chain of the antibody, Or with A genetic sequence coding for a heavy chain of an antibody, with the introduced variant of the OB-fold domain at the 3' end of such light chain.

A genetic sequence coding for the heavy chain of the antibody

A genetic sequence coding for the light chain of the antibody, Or with

A genetic sequence coding for a heavy chain of an antibody, with the introduced variant of the OB-fold domain at the 5' end of such light chain.

A genetic sequence coding for the heavy chain of the antibody

A genetic sequence coding for the light chain of the antibody.

Production of Multi-Specific Molecules

In another embodiment, one shall introduce, within the cell:

A genetic sequence coding for a light chain of an antibody, with a variant of an OB-fold domain introduced at the 5' end of such light chain.

A genetic sequence coding for the heavy chain of the antibody, with a variant of an OB-fold domain introduced at the 5' end of such heavy chain.

The resulting molecule will be, after association of the heavy and light chains, a multi-specific molecule, binding to the antigen of the antibody and to the targets of the variants of the OB-fold domains, said variants of the OB-fold domains being at the N-terminus of the light chains and at the N-terminus of the heavy chains.

It is to be noted that the resulting molecules shall have six binding sites (the two antibody Fab binding sites, and the binding sites of the each of the four variants of the OB-fold domains at the N-terminus of the light chains and at the N-terminus of the light chain), as depicted in FIG. 1.G.

In another embodiment, one shall introduce, within the cell:

A genetic sequence coding for a light chain of an antibody, with a variant of an OB-fold domain introduced at the 3' end of such light chain.

A genetic sequence coding for the heavy chain of the antibody, with a variant of an OB-fold domain introduced at the 5' end of such heavy chain.

The resulting molecule will be, after association of the heavy and light chains, a multi-specific molecule, binding to the antigen of the antibody and to the targets of the variants of the OB-fold domains, said variants of the OB-fold domains being at the C-terminus of the light chains and at the N-terminus of the heavy chains.

It is to be noted that the resulting molecules shall have six binding sites (the two antibody Fab binding sites, and the binding sites of the each of the four variants of the OB-fold domains at the C-terminus of the light chains and at the N-terminus of the light chains), as depicted in FIG. 1.E.

In another embodiment, one shall introduce, within the cell:

A genetic sequence coding for a light chain of an antibody, with a variant of an OB-fold domain introduced at the 5' end of such light chain.

A genetic sequence coding for the heavy chain of the antibody, with a variant of an OB-fold domain introduced at the 3' end of such heavy chain.

The resulting molecule will be, after association of the heavy and light chains, a multi-specific molecule, binding to the antigen of the antibody and to the targets of the variants of the OB-fold domains, said variants of the OB-fold domains being at the N-terminus of the light chains and at the C-terminus of the heavy chains.

It is to be noted that the resulting molecules shall have six binding sites (the two antibody Fab binding sites, and the binding sites of the each of the four variants of the OB-fold domains at the N-terminus of the light chains and at the C-terminus of the light chains), as depicted in FIG. 1.1.

In another embodiment, one shall introduce, within the cell:

A genetic sequence coding for a light chain of an antibody, with a variant of an OB-fold domain introduced at the 3' end of such light chain.

A genetic sequence coding for the heavy chain of the antibody, with a variant of an OB-fold domain introduced at the 3' end of such heavy chain.

The resulting molecule will be, after association of the heavy and light chains, a multi-specific molecule, binding to the antigen of the antibody and to the targets of the variants of the OB-fold domains, said variants of the OB-fold domains being at the C-terminus of the light chains and at the C-terminus of the heavy chains.

It is to be noted that the resulting molecules shall have six binding sites (the two antibody Fab binding sites, and the binding sites of the each of the four variants of the OB-fold domains at the C-terminus of the light chains and at the C-terminus of the light chains), as depicted in FIG. 1.K.

In another embodiment, one shall introduce, within the cell:

A genetic sequence coding for a light chain of an antibody, with a variant of an OB-fold domain introduced at the 5' end of such sequence coding for the light chain and a variant (identical or different) an OB-fold domain introduced at the 3' end of such sequence coding for the light chain A genetic sequence coding for the heavy chain of the antibody.

The resulting molecule will be, after association of the heavy and light chains, a multi-specific molecule, binding to the antigen of the antibody and to the targets of the variants of the OB-fold domains, said variants of the OB-fold domains being at the N- and C-terminus of the light chains.

It is to be noted that the resulting molecules shall have six binding sites (the two antibody Fab binding sites, and the binding sites of the each of the four variants of the OB-fold domains at the N- and C-terminus of the light chains), as depicted in FIG. 1.J.

In another embodiment, one shall introduce, within the cell:

A genetic sequence coding for a heavy chain of an antibody, with a variant of an OB-fold domain introduced at the 5' end of such sequence coding for the heavy chain and a variant (identical or different) an OB-fold domain introduced at the 3' end of such sequence coding for the heavy chain A genetic sequence coding for the light chain of the antibody.

The resulting molecule will be, after association of the heavy and light chains, a multi-specific molecule, binding to the antigen of the antibody and to the targets of the variants of the OB-fold domains, said variants of the OB-fold domains being at the N- and C-terminus of the heavy chains.

It is to be noted that the resulting molecules shall have six binding sites (the two antibody Fab binding sites, and the binding sites of the each of the four variants of the OB-fold domains at the N- and C-terminus of the heavy chains), as depicted in FIG. 1.F.

In the embodiments above, the variants of the OB-fold domains introduced at the termini of the heavy and light chains are either the same or are different.

When the variants are different, they can:

be based on different OB-fold domains and bind the same target be based on different OB-fold domains and bind different targets be based on the same OB-fold domain and bind different targets be based on the same OB-fold domain and bind the same targets (having different mutations).

The cell may also be transformed or transfected with other coding sequences, so as to obtain non-symmetrical molecules.

Other Embodiments for Producing Multi-Specific Molecules

Three Genetic Sequences

In further embodiments, the cells are transformed or transfected with three genetic sequences:

(i) a genetic sequence coding for a light chain of an antibody (ii) a genetic sequence coding for the heavy chain of the antibody, fused to a genetic sequence coding for a variant (A) of an OB-fold domain (at the 3' or 5' end)

(iii) A genetic sequence coding for the heavy chain of the antibody, fused to a genetic sequence coding for another variant (B) of an OB-fold domain (at the 3' or 5' end).

In another embodiment, the three genetic sequences are (i) a genetic sequence coding for a heavy chain of an antibody (ii) a genetic sequence coding for the light chain of the antibody, fused to a genetic sequence coding for a variant (A) of an OB-fold domain (at the 3' or 5' end)

(iii) A genetic sequence coding for the light chain of the antibody, fused to a genetic sequence coding for another variant (B) of an OB-fold domain (at the 3' or 5' end).

The cells will thus produce three different types of multi-specific proteins, at the theoretical following proportions:

A bi-specific protein (binding to the antigen of the antibody and the target of variant (A)): 25%

A bi-specific protein (binding to the antigen of the antibody and the target of variant (B)): 25%

A tri-specific protein (binding to the antigen of the antibody and the targets of variant (A) and (B)): 25%

As for above, variants (A) and (B) of the OB-fold domains can be the same or different.

When the variants are different, they can:

be based on different OB-fold domains and bind the same target be based on different OB-fold domains and bind different targets be based on the same OB-fold domain and bind different targets be based on the same OB-fold domain and bind the same targets (having different mutations).

Multi-Fused Genetic Sequences

It is also possible to fuse genetic sequences coding for variants of OB-fold domains at both the 5' and 3' ends of the genetic sequence coding for the light or the heavy chain of an antibody.

The genetic sequences therein fused can code for the same or different variants, as indicated above.

Specific embodiments are:

To produce proteins having six binding sites (if symmetrical, these proteins would thus be quadri-specific if the OB-fold variants are different).

A genetic sequence coding for a heavy chain of an antibody, with a variant of an OB-fold domain introduced at the 5' end of such sequence coding for the heavy chain and a variant (identical or different) an OB-fold domain introduced at the 3' end of such sequence coding for the heavy chain A genetic sequence coding for the light chain of the antibody, with a variant of an OB-fold domain introduced at the 5' end of such sequence coding for the light chain, thereby leading to a protein as depicted in FIG. 1.N.

A genetic sequence coding for a light chain of an antibody, with a variant of an OB-fold domain introduced at the 5' end of such sequence coding for the light chain and a variant (identical or different) an OB-fold domain introduced at the 3' end of such sequence coding for the light chain A genetic sequence coding for the heavy chain of the antibody, with a variant of an OB-fold domain introduced at the 5' end of such sequence coding for the heavy chain, thereby leading to a protein as depicted in FIG. 1.O.

A genetic sequence coding for a heavy chain of an antibody, with a variant of an OB-fold domain introduced at the 5' end of such sequence coding for the heavy chain and a variant (identical or different) an OB-fold domain introduced at the 3' end of such sequence coding for the heavy chain A genetic sequence coding for the light chain of the antibody, with a variant of an OB-fold domain introduced at the 3' end of such sequence coding for the light chain, thereby leading to a protein as depicted in FIG. 1.M.

A genetic sequence coding for a light chain of an antibody, with a variant of an OB-fold domain introduced at the 5' end of such sequence coding for the light chain and a variant (identical or different) an OB-fold domain introduced at the 3' end of such sequence coding for the light chain A genetic sequence coding for the heavy chain of the antibody, with a variant of an OB-fold domain introduced at the 3' end of such sequence coding for the heavy chain, thereby leading to a protein as depicted in FIG. 1.L.

Transforming or transfecting cells with these genetic sequences leads to a multi-specific protein presenting eight binding sites (the two antibody Fab binding sites, and the six binding sites of the variants of the OB-fold domains.

One can also obtain a protein having ten binding sites by transforming or transfecting cells with A genetic sequence coding for a heavy chain of an antibody, with a variant of an OB-fold domain introduced at the 5' end of such sequence coding for the heavy chain and a variant (identical or different) an OB-fold domain introduced at the 3' end of such sequence coding for the heavy chain A genetic sequence coding for the light chain of the antibody, with a variant of an OB-fold domain introduced at the 5' end of such sequence coding for the light chain and a variant (identical or different) an OB-fold domain introduced at the 3' end of such sequence coding for the light chain, thereby leading to a protein as depicted in FIG. 1.H.

As described above, in all embodiments, the variants of the OB-fold domains can be the same or different.

When the variants are different, they can:
be based on different OB-fold domains and bind the same target
be based on different OB-fold domains and bind different targets
be based on the same OB-fold domain and bind different targets
be based on the same OB-fold domain and bind the same targets (having different mutations).

It is further foreseen that the cells are transformed or transfected with multiple genetic sequences as described above, thereby leading to a mixture of various multi-specific proteins (some of them being non-symmetrical).

Use of the Molecules

Targets and uses can be found on Table I of Fan et al. Journal of Hematology & Oncology (2015) 8:130, which is herein incorporated by reference. Any combination of the targets listed in this table for bi-specific antibodies can be used in the multi-specific molecules herein disclosed. Also are described targets and uses in Yang et al (Int J Mol Sci. 2017 January; 18(1):48) which is also incorporated by reference. In particular, the combinations of targets and potential uses are described below.

Since cytotoxic T lymphocytes play an important role in the immune response against cancer and tumor cell may escape immune response, one strategy is to use bi-specific molecules to recruit the T-cells in the vicinity of the tumor cells. The activation and proliferation of T cells leads to tumor cells lysis.

One target of the multi-specific molecule is a tumor-associated antigen, the second being the CD3 on T cells. It is also possible to also bind type I (CD64), IIa (CD32a), III Fcγ (CD16) receptor (FcγR) on accessory cells such as macrophages, dendritic cells, and NK cells to improve immune response.

Cancer Immunotherapy

| Target 1 | Target 2 | Example of clinical use | Reference antibody |
| --- | --- | --- | --- |
| Any tumor-associated antigen | CD3 | Directing T cells to tumor cells for immunotherapy | Triomabs (the chimeric Fc region preferentially recognizing type I (CD64), IIα (CD32a), III Fcγ (CD16) receptor (FcγR), potential third targets) |
| EpCAM | CD3 | malignant ascites (metastazing cancers) ovarian cancer, gastrointestinal cancer, non-small cell lung cancer, breast cancer, and peritoneal carcinomatosis | Catumaxomab |
| HER2/neu | CD3 | metastatic breast cancer | Ertumaxomab |
| CD20 | CD3 | CD20-positive B cell malignancies | FBTA05 |
| CD19 | CD3 | CD19-expressing B cell malignancies acute B cell lymphoblastic leukemia acute lymphoblastic leukemia (ALL) diffuse large B cell lymphoma (DLBCL) non-Hodgkin lymphoma (NHL) Philadelphia chromosome-negative relapsed or refractory acute lymphoblastic leukemia | Blinatumomab |
| EpCAM | CD3 | solid tumors | Solitomab |
| CEA | CD3 | gastrointestinal adenocarcinoma colorectal cancer colorectal adenocarcinomas | Amg 211/MEDI-565 |
| PSMA | CD3 | Prostate cancer | Amg212/BAY2010112 |
| CD123 | CD3 | acute myeloid leukemia (AML), intermediate-2/high risk myelodysplastic syndromes (MDS) | MGD006 |
| glycoprotein A33 antigen (gpA33) | CD3 | relapsed/refractory metastatic colorectal carcinoma | MGD007 |
| CD19 | CD3 | non-Hodgkin's lymphoma and ALL (acute lymphoblastic leukemia) | AFM11 |
| EpCAM | CD3 | Solid tumors | MT-110 |
| CEA (carcino-embryonic antigen) | CD3 | colorectal cancer colorectal adenocarcinomas | MT-111 |
| CLDN6 (fetal tight junction molecule claudin), highly expressed in various solid tumors | CD3 | Solid tumors | Stadler et al OncoImmunology. 2015; 5: e1091555. |

-continued

| Target 1 | Target 2 | Example of clinical use | Reference antibody |
|---|---|---|---|
| CD33 | CD3 | acute myeloid leukemia | Reusch et al Clin. Cancer Res. 2016; 22: 5829-5838 |
| CD19 | CD3 | CD19+ tumors | Reusch et al mAbs. 2015; 7: 584-604 |

Modifying the Host Response Against Drug Resistance/Metabolic Pathways

Bispecific antibodies are the best choice in that they can simultaneously inhibit two correlated signaling molecules, and in particular inhibitory checkpoint molecules, the main inhibitory factors that hinder immunotherapy.

| Target 1 | Target 2 | Example of clinical use | Reference antibody |
|---|---|---|---|
| CD30 | CD16A | NK cell-mediated immunotherapy, such as Hodgkin's lymphoma | AFM13 |
| HER2 | HER3 | Various cancers including HER2 pathway (HER2 solid tumors) | MM-111 |
| insulin-like growth factor I receptor (IGF-IR) | HER3 | hepatocellular carcinoma | MM-141 |
| EGFR | HER3 | head and neck and colorectal cancers epithelial tumors and neck squamous cell carcinoma (in particular metastatic) | Duligotuzumab |
| HER2 | CD16 | HER2-positive tumor cells | Li et al. AMB Expr (2016) 6: 32 |
| EpCAM | CD16 | Colorectal carcinoma | Schmol et al Mol. Ther. 2016; 24: 1312 |
| B7-H3 | CD3 | Cancer immunotherapy | Ma et al, Oncotarget. 2016 May 17; 7(20): 29480-29491. |
| Met Oncogene | HER2 | Various cancers | Lee et al, Oncogene. 2016; 35: 4437-4446 |
| Met Oncogene | EGFR | Various cancers | Lee et al, Oncogene. 2016; 35: 4437-4446 |
| EGFR | c-Met | Non-small cell lung cancers | Moores et al Cancer Res. 2016; 76: 3942-3953. |

HER2 is a validated target for numerous cancers. HER3 signaling is an important mechanism of drug resistance to HER2 inhibitor. Dual targeting of HER2/HER3 can lead to a more effective response.

Deregulated EGFR- and HER3-dependent signaling is involved in the pathogenesis of human cancers such as head and neck and colorectal cancers.

Targeting HER2 and HER3 restored the sensitivity of GDC-0941 and allowed the GDC-0941 to again stop the growth of the prostate cancer (Poovassery et al, Int. J. Cancer. 2015; 137:267-277).

Anti-Angiogenesis

| Angiogenic factor such as endothelial growth factor receptor 2 (VEGFR2), VEGFR3, endothelial growth factor A (VEGFA), angiopoietins, and platelet-derived growth factors (PDGFs) | Tumor antigen or angiogenic factor | Cancers | |
|---|---|---|---|
| VEGFA | Angiopoietin 2 | colorectal cancer | RG7221 |
| VEGFA | Angiopoietin 2 | wet type age-related macular degeneration (wet AMD) | RG7716 |
| VEGF | Angiopoietin 2 | glioblastoma | Kloepper et al Proc. Natl. Acad. Sci. USA. 2016; 113: 4476-4481 |
| VEGF | DLL4 (Δ-like ligand 4 (DLL4)) | | HD105 (Lee et al, mAbs. 2016; 8: 892-904) |

Multiple angiogenic factors including endothelial growth factor receptor 2 (VEGFR2), VEGFR3, endothelial growth factor A (VEGFA), angiopoietins, and platelet-derived growth factors (PDGFs) are involved in tumor angiogenesis. Many cancer therapies disrupt angiogenesis by depleting these proteins Dual targeting of angiogenic factors leads to superior outcomes [Biel and Siemann Cancer Lett. 2016 Oct. 1; 380(2):525-33)

Adoptive T Cell Transfer for Cancer Immunotherapy

Targets would be PD-1, tumor antigens, molecules expressed at the surface of T lymphocytes.

Presence of the bispecific molecules in vitro with the cancer cells, and T lymphocytes would allow efficient priming of the T lymphocytes that can later be injected to the patient.

Bispecific PD-1/CD3, tumor antigen/CD3, HER2/CD3 can be used. One can also follow the teachings of Urbanska et al (J. Transl. Med. 2014; 12:347, which uses bispecific antibodies (CD20/CD3 or HER2/CD3) and engineered T cells.

Binding to Cytokines

| Cytokines Target 1 | Target 2 | Example of clinical use | Reference antibody |
|---|---|---|---|
| TNF-α | HSA | rheumatoid arthritis (RA) | Ozoralizumab |
| IL6R | HSA | rheumatoid arthritis (RA) | ALX-0061 |
| IL13 | IL4 | idiopathic pulmonary fibrosis | SAR156597 |

Several cytokines have been identified as key mediators of inflammatory and autoimmune diseases. Therefore, blockage of these cytokines has treatment potential. For example, the inhibition of TNF-α exerts profound therapeutic effects on psoriasis, psoriatic arthritis, Crohn's disease, ulcerative colitis, juvenile arthritis, and many other diseases. Other validated cytokines include IL-6, IL-17, IL-1, IL-12, TGF-8, IL-4, and IL-13.

Delivery of Payloads

| Target 1 | Target 2 | Example of clinical use | Reference antibody |
| --- | --- | --- | --- |
| TNF-α | HSA | rheumatoid arthritis (RA) | Ozoralizumab |
| IL6R | HSA | rheumatoid arthritis (RA) | ALX-0061 |
| IL13 | IL4 | idiopathic pulmonary fibrosis | SAR156597 |
| Digoxigenin (for capture of digoxigeninylated compounds) | cell membrane antigens (such as HER2) | | Metz et al Proc. Natl. Acad. Sci. USA. 2011; 108: 8194-8199 |

An interesting application is the delivery of payloads such as drugs, radiolabels, and nanoparticles. The payloads are administered once the unbound bispecific molecules are cleared from the bloodstream. Bispecific molecules can be used to enrich payloads in tumor sites. This strategy significantly prolongs the serum retention time and improves the tumor/blood ratio. One can cite the bispecific TF2 built used for tumor imaging and radioimmunotherapy, which specifically binds to CEA and $^{99m}$T-labeled hapten histamine-succinyl-glycine (HSG). In the preclinical trial, TF2 was first injected, and $^{99m}$T-labeled HSG was then administered after the clearance of the bsAb from the blood. A high tumor/blood ratio was observed with high tumor uptake of $^{99m}$T. TF2 is in phase I study in patients with colorectal cancer. Other applications of TF2 include targeting against $^{177Lu}$HSG/$^{111In}$HSG and CEA for radioimmunotherapy in patients with colorectal neoplasms and targeting against $^{68Ga}$HSG and CEA for immuno-positron emission tomography (from Fan et al. Journal of Hematology & Oncology (2015) 8:130).

Digoxigenin (Dig), as a hapten, can be used as the payload scaffold to embark on some cytotoxic moieties, such as fluorophores, chelating agents, chemotherapeutics, nucleic acids, lipids, nanoparticles or peptides and proteins, and finally, form compounds, like Dig-Cy5, Dig-doxorubicin and Dig-GFP. It was also shown that hapten-based bispecific antibody is also an effective siRNA delivery system, and in particular siRNA, digoxigeninylated at its 3'-end and formulated into nanoparticles was bound to bispecific antibodies, binding tumor antigens, such as HER2, IGF1-R, CD22 and LeY, which delivered siRNAs specifically to cells expressing the corresponding antigen and led to internalization into endosomes and separation of Dig-siRNAs from bispecific antibodies (Schneider et al, Mol. Ther. Nucleic Acids. 2012; 1:e45).

Bacterial minicells are anucleate nanoparticles produced by inactivation of the genes that control normal bacterial cell division. Chemotherapeutic drugs can be packaged into minicells that are then linked to a bi-specific molecule also binding an antigen on the membrane of a cell (such as a cancer cell), which results in endocytosis, intracellular degradation and drug release (Solomon et al, PLoS ONE. 2015; 10:e0144559).

Crossing the Blood-Brain Barrier

| Target 1 | Target 2 | Example of clinical use | Reference antibody |
| --- | --- | --- | --- |
| TfR | β-site APP-cleaving enzyme 1 (BACE1) | Alzheimer disease | Couch et al, Sci Transl Med. 2013 May 1; 5(183): 183ra57, 1-12, Yu et al, Sci Transl Med. 2014 Nov. 5; 6(261): 261ra154 |

Couch et al, and Yu et al. designed bsAb that binds to transferrin receptor (TfR) and β-site APP-cleaving enzyme 1 (BACE1) and cross the Blood-brain barrier.

Diagnostic Assays

| Target 1 | Target 2 | Example of clinical use | Reference antibody |
| --- | --- | --- | --- |
| Specific antigen (bacterial, viral, tumor, parasitic . . .) | Detecting moiety (horseradish peroxidase, GFP, radioactive tracer . . .) | Presence of the specific antigen | |

Treatment of Infectious Diseases

| Target 1 | Target 2 | Example of clinical use | Reference antibody |
| --- | --- | --- | --- |
| Infectious agent antigen (bacterial, viral, parasitic . . .) | Infectious agent, Immune cell antigen | Treatment of infectious disease | |
| PsI, polysaccharide that plays a role in immune evasion and biofilm formation | PcrV, involved in the secretion of virulence factors | *Pseudomonas aeruginosa* infections | BiS4αPa (MEDI3902) DiGiandomenico et al, Sci. Transl. Med. 2014; 6: 262ra155 Thaden et al, J. Infect. Dis. 2016; 213:640-648 |
| HIV antigen (such as gp120) | Immune cell antigen (such as CD3) | HIV treatment | Berg et al, Proc Natl Acad Sci. 1991; 88(11): 4723-7. |
| HIV antigen | CD4 receptor or CCR5 co-receptor | HIV treatment | Huang et al, Cell. 2016; 165: 1621-1631 |

-continued

| Target 1 | Target 2 | Example of clinical use | Reference antibody |
|---|---|---|---|
| HIV antigen (env) | CD4 receptor | HIV treatment | Bourzanos et al, Cell. 2016; 165: 1609-1620 |
| HBV antigen (S antigen) | HBV antigen (pre-S2 antigen) | Hepatitis B | Park et al Mol Immunol. 2000; 37(18):1123-30. |

Other Uses

| Target 1 | Target 2 | Example of clinical use | Reference antibody |
|---|---|---|---|
| activated coagulation factor IX | Factor X | Decrease bleeding rate in hemophilia A Mimicking Factor VIII | Emicizumab (ACE910) Shima et al N. Engl. J. Med. 2016; 374: 2044-2053 |
| sclerostin | DKK-1 | bone mass accrual and fracture repair | Florio et al Nat. Commun. 2016; 7: 11505 |

Therapeutic Methods

The invention also relates to a multi-specific molecule as described above as a medicament, and/or for its use for treating or preventing a disease where inhibition of the targets is needed. It is clear that the choice of the targets depends on the disease that one wishes to treat or prevent, as illustrated above.

Therapeutic methods are also part of the invention. The invention also encompasses method for treating a patient in need thereof, comprising the step of administering a therapeutically effective amount of a molecule herein disclosed. A "therapeutically effective" amount hereby is defined as the amount that is sufficient to obtain a clinical effect (alleviation of adverse condition). It can be determined by Phase II clinical trials. it may be administered as a single dose or according to a multiple dose regimen, alone or in combination with another agent. It is preferably non-toxic or have a toxicity that is acceptable in view of the benefit to the patient's health. The subject may be a human or non-human animal (e.g., rabbit, rat, mouse, monkey or other lower-order primate).

The molecule herein disclosed shall be formulated using one or more physiologically acceptable carriers or excipients known in the art and be administered by any suitable means and through any suitable route. One thus foresees parenteral (e.g., intramuscular, intravenous, intraarterial, intraperitoneal, or subcutaneous), intrapulmonary and intranasal, and, if desired for local immunosuppressive treatment, intralesional administration. Injections (in particular intravenous injections) are preferred. The route of administration may vary depending on the disease to be treated.

Molecules against TNF-alpha are generally used for treating inflammatory diseases (arthritis, Rheumatoid arthritis, Inflammatory bowel disease, Ulcerative colitis, rhinitis, psoriasis, Crohn's disease) as well as some cancers (colorectal, breast, bladder, glioblastoma, other solid cancers) or other immunological disorders.

Molecules against IL17 are also generally used for treating the same kinds of inflammatory diseases (arthritis, Rheumatoid arthritis, Inflammatory bowel disease, Ulcerative colitis, rhinitis, psoriasis, Crohn's disease, Spondylitis ankylosing) as well as some cancers (colorectal, breast, bladder, glioblastoma, other solid cancers) or other immunological disorders (including multiple sclerosis).

A complex comprising an antibody binding to TNF-alpha and a OB-fold variant (or protein from the Dac7d family) binding to IL17 (or vice-versa) can thus be used for the treatment of such diseases.

Specific Compositions

In particular, the invention relates to a polypeptide as disclosed above, wherein the variant of a protein of the Sac7d family binds to a subunit of TNFalpha. Preferably, it doesn't bind to the subunit of the protein when such subunit protein is involved in the fully formed multimeric protein in its native state.

The inventors have indeed identified that it is possible to identify variants of proteins of the Sac7d family that would bind to a soluble subunit of TNF-alpha, that would then lead to the avoidance of the formation of the biologically active multimeric protein or the shifting of the equilibrium towards the monomeric (or multimeric inactive) subunits.

In particular, such variant comprises the sequence

```
                                              (SEQ ID NO: 39)
MVKVKFXXXGXEKEVDTSKIXXVXRXGKXVHFWYXDNGKIXKGXVXEKDA

PKELLDMLARAEREK
                                              (SEQ ID NO: 40)
MVKVKFXXXGXEKEVDTSKIXHVMRXGKXVHFWYEDNGKIXKGXVXEKDA

PKELLDMLARAEREK
or
                                              (SEQ ID NO: 41)
MVKVKFVMFGKEKEVDTSKIVHVMRQGKLVHFWYXDNGKIDKGFVPEKDA

PKELLDMLARAEREK.
```

In particular, between 1 to 13, preferably from 1 to 11, more preferably from 1 to 10, more preferably from 1 to 8, more preferably from 1 to 6, more preferably from 1 to 5, more preferably from 1 to 4, more preferably from 1 to 3, more preferably 2, more preferably 1 amino acid selected from the group consisting of V7, M8, F9, K11, V21, H22, M24, Q26, L29, E35, D41, F44 and P46, more preferably from the group consisting of V7, M8, F9, K11, V21, Q26, L29, E35, D41, F44 and P46, have been replaced by another amino acid in SEQ ID NO: 41.

In this embodiment, it is preferred when the antibody binds to a protein selected from the group consisting of IL17, CD20, IL24, IL12, IL4, IL13, IL6, IL31 or its receptor and a tumor specific antigen, in particular Her2, PDL1 (Programmed death-ligand 1, CD274) or CTLA4.

In particular the antibody binds to IL17 (and is in particular infliximab, adalimumab, certolizumab pegol, orgolimumab, Secukinumab, Afasevikumab, Bimekizumab, or Vunakizumab).

In particular the antibody binds to CD20 (and is in particular Blontuvetmab, FBTA05, Ibritumomab tiuxetan, Mosunetuzumab, Obinutuzumab, Ocaratuzumab, Ocrelizumab, Ofatumumab, Rituximab, Tositumomab, or Veltuzumab), In particular the antibody binds to IL24.

In particular the antibody binds to IL12.

In particular the antibody binds to IL4 (and is in particular Dupilumab).

In particular the antibody binds to IL13.

In particular the antibody binds to IL6 (and is in particular Siltuximab, Olokizumab, or Vobarilizumab)

In particular the antibody binds to IL31 or its receptor.

In particular the antibody binds to a tumor specific antigen as disclosed above.

In particular the antibody binds to Her2 (and is in particular DS-8201, Ertumaxomab, Gancotamab, Margetuximab, Pertuzumab, Timigutuzumab, Trastuzumab or Trastuzumab emtansine).

In particular the antibody binds to PDL1 (Programmed death-ligand 1, CD274).

In particular the antibody binds to CTLA4 (and is in particular Tremelimumab).

In another embodiment, the variant of a protein of the Sac7d family binds to IL17.

In this embodiment, it is preferred when the variant of a protein of the Sac7d family comprises one of the following sequences Seq id 35

```
                                               SEQ ID NO: 35
MVKVKFXXXGEEKEVDTSKIFNVWRXGKXVNFMYDDNGKIGIGXVXEKDA

PKELLDMLARAEREKK

SEQ ID NO: 36
MVKVKFXXXGEEKEVDTSKIFNVWRXGKSVNFMYDDNGKIGIGXVXEKDA

PKELLDMLARAEREKK.

SEQ ID NO: 37
MVKVKFHAKGEEKEVDTSKIFNVWRSGKSVNFMYDDNGKIGIGHVDEKDA

PKELLDMLARAEREKK
or
                                               SEQ ID NO: 38
MVKVKFSRFGEEKEVDTSKIFNVWRIGKTVNFMYDDNGKIGIGAVDEKDA

PKELLDMLARAEREKK.
```

In this embodiment, it is preferred when the antibody binds to a protein selected from the group consisting of TNFalpha (in particular infliximab, adalimumab, certolizumab pegol, orgolimumab), IL23 (in particular Brazikumab, Guselkumab, Mirikizumab, Risankizumab, or Tildrakizumab), IL12 (in particular Briakinumab, Ustekinumab), IL4 (in particular Dupilumab), IL13 (in particular Anrukinzumab), IL31 or its receptor and a tumor specific antigen, in particular Her2 (in particular DS-8201, Ertumaxomab, Gancotamab, Margetuximab, Pertuzumab, Timigutuzumab, Trastuzumab or Trastuzumab emtansine, PDL1 (Programmed death-ligand 1, CD274) or CTLA4 (in particular Tremelimumab).

In particular the antibody binds to TNFalpha (and is in particular infliximab, adalimumab, certolizumab pegol, orgolimumab).

In particular the antibody binds to IL23 (and is in particular Brazikumab, Guselkumab, Mirikizumab, Risankizumab, or Tildrakizumab).

In particular the antibody binds to IL12 (and is in particular Briakinumab, or Ustekinumab).

In particular the antibody binds to IL4 (and is in particular Dupilumab).

In particular the antibody binds to IL13 (and is in particular Anrukinzumab).

In particular the antibody binds to IL31 or its receptor.

In particular the antibody binds to a tumor specific antigen as disclosed above.

In particular the antibody binds to Her2 (and is in particular DS-8201, Ertumaxomab, Gancotamab, Margetuximab, Pertuzumab, Timigutuzumab, Trastuzumab or Trastuzumab emtansine).

In particular the antibody binds to PDL1 (Programmed death-ligand 1, CD274).

In particular the antibody binds to CTLA4 (and is in particular Tremelimumab).

Specific Variant of Sac7d Binding to IL17

The invention also relates to a polypeptide comprising a variant of a protein of the Sac7d family, the variant comprising between 4 and 22 mutated amino acids in the binding site of the protein of the Sac7d family that binds to IL17, in particular as disclosed herein, as such improves or stabilize the production of antibodies. It is reminded that the sequence of Sac7d is:

```
                                               (SEQ ID NO: 1)
MVKVKFKYKGEEKEVDTSKIKKVWRVGKMVSFTYDDNGKTGRGAVSEKDAP

KELLDMLARAEREKK.
```

It is possible to obtain the above polypeptide, wherein the mutated amino acids of the Sac7d variant are selected from the group consisting of V2, K3, K5, K7, Y8, K9, G10, E11, K13, E14, T17, K21, K22, W24, V26, G27, K28, M29, S31, T33, Y34, D35, D36, N37, G38, K39, T40, G41, R42, A44, S46, E47, K48, D49, A50 and P51 of Sac7d.

It is possible to obtain the above polypeptide, wherein the Sac7d variant contains 4 to 17 mutated amino acids selected from the group corresponding to K7, Y8, K9, E11, K21, K22, W24, V26, M29, S31, T33, D35, T40, G41, R42, A44, and S46 of Sac7d.

In this embodiment, it is preferred when the variant of a protein of the Sac7d family comprises one of the following sequences Seq id 35

```
                                               SEQ ID NO: 35
MVKVKFXXXGEEKEVDTSKIFNVWRXGKXVNFMYDDNGKIGIGXVXEKDA

PKELLDMLARAEREKK

SEQ ID NO: 36
MVKVKFXXXGEEKEVDTSKIFNVWRXGKSVNFMYDDNGKIGIGXVXEKDA

PKELLDMLARAEREKK.
```

-continued

SEQ ID NO: 37
MVKVKFHAKGEEKEVDTSKIFNVWRSGKSVNFMYDDNGKIGIGHVDEKDA

PKELLDMLARAEREKK or

SEQ ID NO: 38
MVKVKFSRFGEEKEVDTSKIFNVWRIGKTVNFMYDDNGKIGIGAVDEKDA

PKELLDMLARAEREKK.

In particular such polypeptide comprises the sequence SEQ ID NO: 37 or SEQ ID NO: 38, in which from 1 to 10, more preferably from 1 to 8, more preferably from 1 to 6, more preferably from 1 to 5, more preferably from 1 to 4, more preferably from 1 to 3, more preferably 2, more preferably 1 amino acid selected from the group consisting of V7, M8, F9, K11, Q26, L29, E35, D41, F44 and P46 have been replaced by another amino acid. Indeed, the applicant has shown that such residues may be modified without changing the observed binding. This was performed by changing these residues with an Alanine and checking the binding. Since there was no loss of binding, this indicates that these residues are not important for the binding to IL17.

In a specific embodiment, said specific Sac7d variant is linked or fused to another protein or polypeptide. In particular, said other protein or polypeptide comprises another variant of a protein of the Sac7d family. As indicated above, it is also foreseen when the other protein or polypeptide is an antibody, preferably binding to TNF-alpha or Her2/neu.

In another embodiment, this variant of the Sac7d family is conjugated to an organic molecule. This may be done by any method known in the art. In particular, one can chemically link the molecule to the protein. As a molecule, one can cite antiproliferative (cytotoxic and cytostatic agents) include cytotoxic compounds (e.g., broad spectrum), angiogenesis inhibitors, cell cycle progression inhibitors, PBK/m-TOR/AKT pathway inhibitors, MAPK signaling pathway inhibitors, kinase inhibitors, protein chaperones inhibitors, HDAC inhibitors, PARP inhibitors, Wnt/Hedgehog signaling pathway inhibitors, RNA polymerase inhibitors and proteasome inhibitors. One can also use anti-inflammatory molecules.

One can cite in particular DNA-binding or alkylating drugs such as anthracyclines (doxorubicin, epirubicin, idarubicin, daunorubicin) and its analogs, alkylating agents, such as calicheamicins, dactinomycines, mitromycines, pyrrolobenzodiazepines, and the like. One can also cite cell cycle progression inhibitors such as CDK inhibitors, Rho-kinase inhibitors, checkpoint kinase inhibitors, aurora kinase inhibitors, PLK inhibitors, and KSP inhibitors. One can also cite thalidomide and its derivatives lenalidomide and pomalidomide. In order for treating inflammation disorders, one can also use cyclooxygenase-2 inhibitors, inhibitors, quercetin and/or resveratrol as molecules conjugated to the polypeptide comprising the variant.

The invention also relates to a genetic construct comprising a DNA sequence coding for the polypeptide as herein disclosed (variant of a protein of the Sac7d family, binding to IL17).

The invention also relates to a vector comprising the genetic construct disclosed above, a host cell comprising such genetic construct in its genome, and a method for producing such variant of the protein of the Sac7d family binding to IL17, comprising the steps consisting of a. Culturing a cell culture wherein the cells have been transformed by a genetic construct as disclosed, And b. Recovering the polypeptide.

Sequence of the identified variant can be cloned in any appropriate vector by any molecular genetic methods known in the art.

These recombinant DNA constructs comprising a nucleotide sequence, coding for a polypeptide comprising a variant as described above, are used in connection with a vector, such as a plasmid, phagemid, phage or viral vector.

These recombinant acid molecules can be produced by techniques described in Sambrook et al., 1989 (Sambrook J, Fritschi E F and Maniatis T (1989) Molecular cloning: a laboratorymanual, Cold Spring Harbor Laboratory Press, New York). Alternatively, the DNA sequences may be chemically synthesized using, for example, synthesizers.

Recombinant constructs of the invention comprise the expression vectors that are capable of expressing the RNA and thus lead to production of proteins from the above genetic sequences. The vector may thus further comprise regulatory sequences, including a suitable promoter operably linked to the open reading frame (ORF) of the genetic sequences herein disclosed. The vector may further comprise a selectable marker sequence such as an antibiotic resistance gene. Specific initiation and bacterial secretory signals also may be required for efficient translation of the coding sequences when bacteria as used as the expression host.

Production of the Molecules

Cells are transfected or transformed with vectors containing the sequences coding for the polypeptides comprising the variant as disclosed above.

The cells are the cultured in such conditions as to have the protein expressed and favorably secreted. The conditions of culture of the cells are the conditions generally used for recombinant antibody production and are known in the art. Such conditions that are known in the art can also be optimized by the person skilled in the art if needed. Kunert and Reinhart (Appl Microbiol Biotechnol. 2016; 100: 3451-3461) review such methods and provide ample references thereto.

One can use bacterial, phage (Shukra et al, Eur J Microbiol Immunol (Bp). 2014; 4(2): 91-98) or eukaryotic systems of production.

One shall prefer to use eukaryotic cells in order to obtain proper post-translational modifications such as glycosylation.

In particular, one can use CHO (Chinese Hamster Ovary) cells, PER.C6 cells (human cell line, Pau et al, Vaccine. 2001 21; 19(17-19):2716-21), HEK 293b cells (Human embryonic kidney cells 293), NS0 cells (cell line derived from the non-secreting murine myeloma) or EB66 cells (a duck cell line Valneva, Lyons, France).

Also provided by the present disclosure are host cells containing at least one of the DNAs constructs coding for a polypeptide comprising the variant as disclosed herein. The host cell can be any cell for which expression vectors are available. As indicated above, it may be a higher eukaryotic host cell, such as a mammalian cell, a lower eukaryotic host cell, such as a yeast cell, or a prokaryotic cell, such as a bacterial cell.

Introduction of the recombinant construct into the host cell is performed by any method known in the art (such as calcium phosphate transfection, lipofection, DEAE, dextran mediated transfection, electroporation or phage infection). The vectors can be inserted within the genome of the host cell, or be maintained as an extragenomic vector (such as a Bacterial Artificial Chromosome or a Yeast Artificial Chromosome). When introduced within the cell genome, such introduction may be random or targeted using methods known in the art (homologous recombination or the like).

Bacterial Hosts and Expression

Useful expression vectors for bacterial use are constructed by inserting the recombinant DNA sequence together with suitable translation initiation and termination signals in operable reading phase with a functional promoter. The vector will comprise one or more phenotypic selectable markers and an origin of replication to ensure maintenance of the vector and, if desirable, to provide amplification within the host.

Suitable prokaryotic hosts for transformation include *E. coli, Bacillus subtilis, Salmonella typhimurium* and various species within the genera *Pseudomonas, Streptomyces*, and *Staphylococcus*.

Eukaryotic Hosts and Expression

Examples of the eukaryotic host cells include vertebrate cells, insect cells, and yeast cells. In particular, one can use the cells mentioned above.

The transformed or transfected cells are cultured according to methods known in the art and the polypeptide are recovered from intracellular or extracellular fractions (depending on whether it is secreted or not).

Isolation of the Molecules

The recombinant multi-specific protein produced can be separated and purified by any of various known separation methods utilizing the physical or chemical property of the protein, from the intracellular or extracellular fraction.

In particular, one can use methods such as precipitation, ultrafiltration, various types of liquid chromatography such as molecular sieve chromatography (gel filtration), adsorption chromatography, ion exchange chromatography, and affinity chromatography, dialysis, and a combination thereof.

In general, any method known and used to purify recombinant polypeptides is adapted for the purification of the molecules herein disclosed.

If a tag has been introduced within the recombinant sequence (such as a poly-Histidine tag), one can purify the molecules using this tag. However, it is preferred to use affinity to purify the molecules.

One can, in particular, use the fact that the molecule herein produced binds to a specific target and use any affinity method (affinity column, FACS, beads) to isolate such molecules.

One particular advantage of the molecules herein disclosed is that they don't need to be glycosylated to be active and can thus be produced in any type of cells, and not necessarily eukaryotic cells. They are particularly well produced in bacterial cells.

The invention also relates to such a variant of a protein of the Sac7d family, binding to IL17 as a medicament.

EXAMPLES

Figure 1:
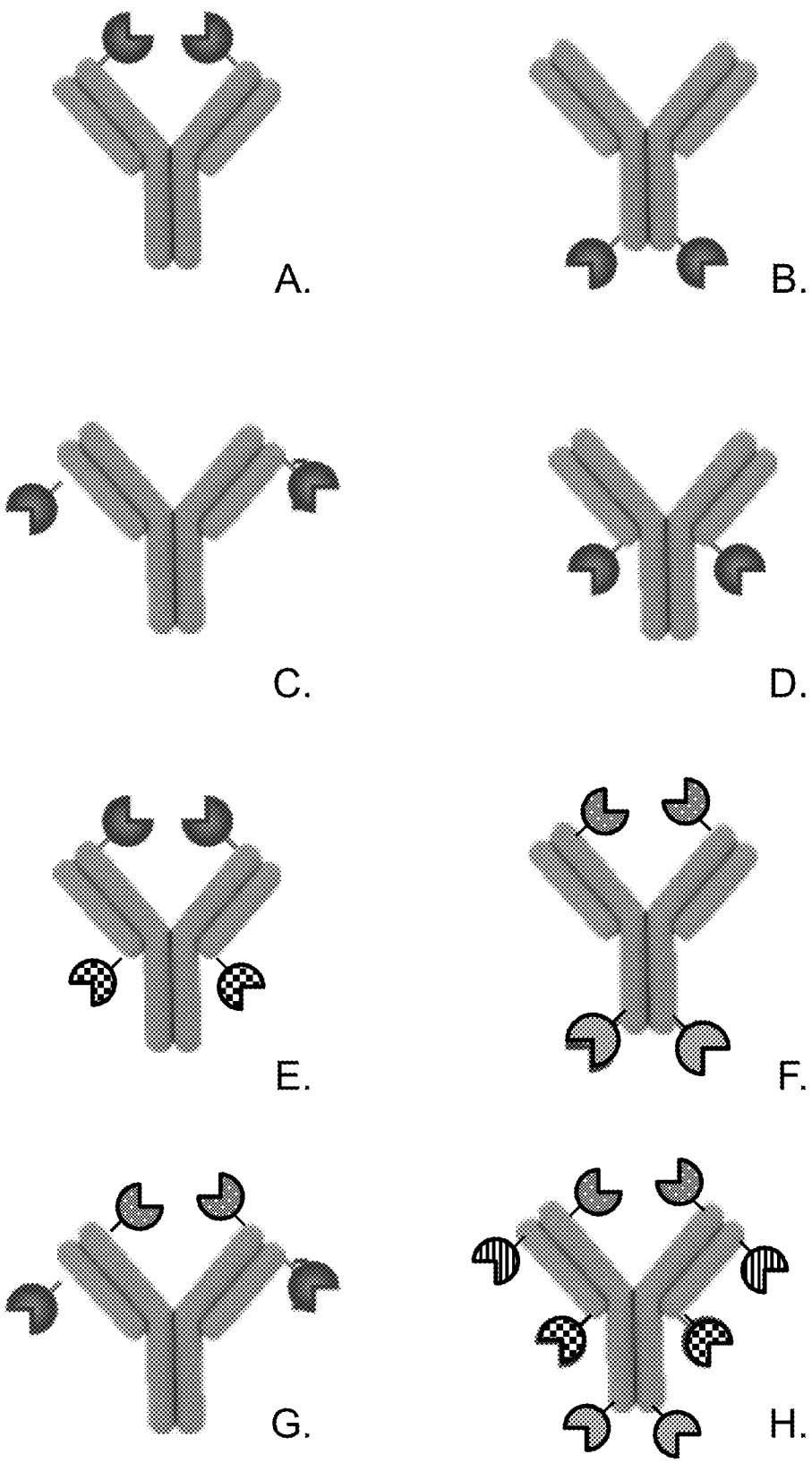
FIG. 1: schematic representation of 15 proteins according to the invention. These proteins are symmetrical. A. OB-fold variant at the N-term of heavy chain. A. OB-fold variant at the C-term of heavy chain. C. OB-fold variant at the N-term of light chain. D. OB-fold variant at the C-term of light chain. E. OB-fold variant at the N-term of heavy chain and C-term of light chain. F. OB-fold variant at the N- and C-term of heavy chain. G. OB-fold variant at the C-term of heavy chain and N-term of light chain. H. OB-fold variant at the N- and C-term of heavy and light chains. I. OB-fold variant at the N-term of heavy chain and N-term of light chain. J. OB-fold variant at the N- and C-term of light chain. K. OB-fold variant at the C-term of heavy chain and C-term of light chain. L. OB-fold variant at the C-term of heavy chain and N- and C-term of light chain. M. OB-fold variant at the N- and C-term of heavy chain and C-term of light chain. N. OB-fold variant at the N- and C-term of heavy chain and N-term of light chain. O. OB-fold variant at the N-term of heavy chain and N- and C-term of light chain.
Figure 1:
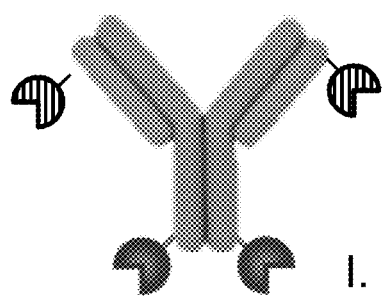
Figure 1:
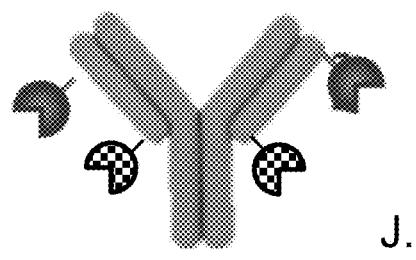
Figure 1:
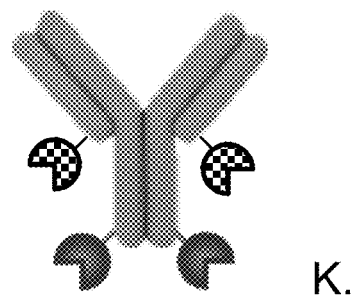
Figure 1:
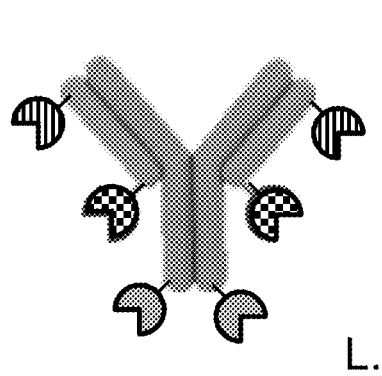
Figure 1:
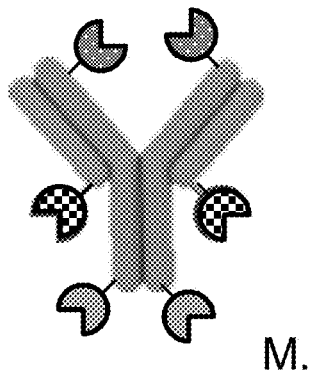
Figure 1:
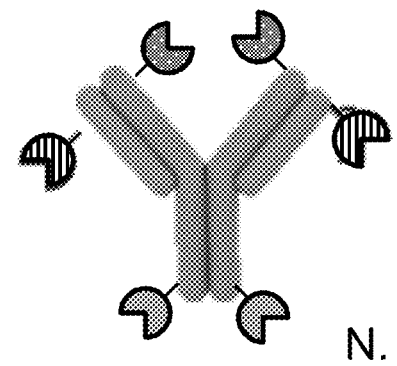
Figure 1:
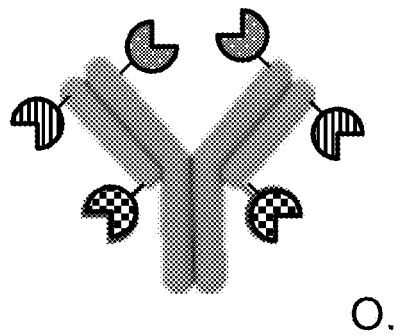

Bi-specific antibodies made by the genetic fusion of an OB-fold can result in four different bi-specific constructs when the OB-fold is inserted at either the N- or C-terminus of either the heavy or light chain. Experiments below exemplify the fusion of a variant of Sac7d variant to an IgG1 kappa antibody. These experiments are to demonstrate the proof of concept, and that it is possible to maintain the binding specificities of both the antibody fragment and the OB-fold variant, and the level of production of the fusion protein (such production being similar or even improved as compared to the antibody yield without the fused OB-fold variant).

The constant fragments of both the heavy and light chain were obtained respectively via the commercial encoding vectors pFUSE-CHIg-hIG1 (InvivoGen) and pFUSE2ss-CLIg-hk (InvivoGen).

The respective variable domains were obtained by gene synthesis (Eurofins).

The DNA encoding sequence of the Sac7d variant was directly amplified by PCR from the product of a sub-cloning in an expression vector derived from pQE30 (Qiagen).

The constant fragment, variable domain and the sequence of the Sac7d variant, when it applies, were then assembled by Gibson Assembly to generate 6 different vectors, three of them deriving from the pFUSE-CHIg-hIG1 vector and the three other form pFUSE2ss-CLIg-hk vector. In all the cases, the vectors were differing by the localization of the sequence of the Sac7d variant at either the upstream (fusion at the N-terminus) or downstream (fusion at the C-terminus) of the sequence of the antibody chains, or its absence (no fusion).

In summary, the six vectors code for:
light chain of the antibody alone
light chain of the antibody fused to Sac7d variant at the N-terminus
light chain of the antibody fused to Sac7d variant at the C-terminus
heavy chain of the antibody alone
heavy chain of the antibody fused to Sac7d variant at the N-terminus
heavy chain of the antibody fused to Sac7d variant at the C-terminus Examples below illustrate the construction of a polypeptide as contemplated herein.

Other such polypeptides have been obtained with other Sac7d variants and antibodies and their analysis gave similar results than the ones reported below (ease of production, binding to both the targets of the Sac7d variant and of the antibody).

The Sac7d variants were generated according to the method disclosed in WO 2008/068637, using ribosome display to isolate the variants against given targets from libraries with up to 14 mutated amino acids.

In summary, more than 7 Sac7d variants were used in various experiments. Each variant bound to a different target or to different epitopes of the same target. These variants had 14 (residues 7, 8, 9, 21, 22, 24, 26, 29, 31, 33, 40, 42, 44, 46), 11 (residues 7, 22, 24, 26, 29, 31, 33, 38, 42, 44, 46), 10 (residues 21, 22, 24, 26, 29, 31, 33, 42, 44, 46), 10 (residues 21, 22, 24, 26, 29, 31, 33, 40, 44, 46), 9 (residues 21, 22, 24, 26, 31, 33, 42, 44, 46) mutated amino acids as compared to Sac7d.

3 antibodies, each binding to a different target or different epitopes of the same target (circulating proteins).

28 combinations of fusion polypeptides were made using similar methods as described below, and the results were all similar.

In particular, the Sac7d variants used were against IL17 (especially SEQ ID NO: 37 and SEQ ID NO: 38) fused to anti-TNF-alpha. Other Sac7d variants (in particular SEQ ID NO: 41 binding to TNF-alpha or SEQ ID NO: 42 binding to lysozyme and referred to as H4) were used. Other Sac7d variants against other targets were also used. As indicated above, the yield of the recovered polypeptide antibody-variant of Sac7d was consistently equal or above the yield of the antibody without the Sac7d variant and the dual affinity was confirmed every time it was checked.

As indicated above, it is hypothesized that the whole structure of the complex may be stabilized by the addition of the Sac7d variant (hence leading to the production improvement). Since both the antibody and the Sac7d variant maintain their structure (as demonstrated by the dual binding assays showing that they retain their functions), it is submitted that the results provided for the various species in the examples can be generalized to whole genus.

Example 1. Fusion to the Heavy Chain (N or C-Terminus)

The description is provided for the construction of the full heavy chains. Fusion of the Sac7d variant sequence at the N-terminus of the full heavy chain consisted in the DNA re-engineering of the pFUSE-CHIg-hIG1 vector by Gibson Assembly, which involves the preparation by PCR amplification of two fragments and a linearized vector.

pFUSE-CHIg-hIG1 was linearized by PCR amplification with the forward oligonucleotide oligoCH-1 (GCTAGCAC-CAAGGGCCCA, SEQ ID NO: 16) and reverse oligonucleotide VHfuse_Rev (TGAATTCGTGACAAGTGCAA-GACT, SEQ ID NO: 17) according to the PCR program 1.

The DNA sequence coding the variable domain was amplified by PCR with the forward oligonucleotide OligoCH-2 (GGTAGTGCAGGCTCCGGCAGTGGCGG-TAGCGAGGTGCAGTTGGTAGAGT, SEQ ID NO 18) and reverse oligonucleotide OligoCH-3 (GCCCTTGGTGCTAGCACT, SEQ ID NO: 19) according to the PCR program 2.

The DNA sequence of the Sac7d variant was amplified by PCR with the forward oligonucleotide VH_NF_For (CTTGTCACGAATTCAGTCAAGGTGAAATTC, SEQ ID NO: 20) and reverse oligonucleotide Glink15.1_Rev (GGAGCCTGCACTACCG-GAACCGCCT-GAACCTTTCTCGCGTTCCGC, SEQ ID NO: 21) according to the PCR program 2.

Fusion of the Sac7d variant sequence at the C-terminus of the full heavy chain involves the preparation by PCR amplification of three fragments and a linearized vector. pFUSE-CHIg-hIG 1 was linearized by PCR amplification with the forward oligonucleotide OligoCH-4 (TGAGTCCTAGCTGGCCAGA, SEQ ID NO: 22) and reverse oligonucleotide IL2ss_Rev (TGAAT-TCGTGACAAGTGCAAGACTTA-GTGCA, SEQ ID NO: 23) according to the PCR program 1.

The DNA sequence of the constant domain was amplified by PCR with the forward oligonucleotide oligoCH-1 (SEQ ID NO: 16) and reverse oligonucleotide OligoCH-5 (GGAGCCTGCACTACCGGAACCGCCTGAACCTT-TACCCGGAGACAGGGAGA, SEQ ID NO: 24) according to the PCR program 2.

The DNA sequence coding the variable domain was amplified by PCR with the forward oligonucleotide OligoCH-6 (CTTGTCACGAATTCAGAGGTG, SEQ ID NO: 25) and reverse oligonucleotide OligoCH-3 (SEQ ID NO: 19) according to the PCR program 2.

The DNA sequence of the Sac7d variant was amplified by PCR with the forward oligonucleotide Glink15.1_For (GGTAGTGCAGGCTCCGGCAGTGGCGGTAGC-GT-CAAGGTGAAATTC, SEQ ID NO: 26) and reverse oligonucleotide OligoCH-7 (GCCAGCTAGGACTCAT-TTCTCGCGTTCCGC, SEQ ID NO: 27) according to the PCR program 2.

Construction of the full heavy chain lacking the fusion with the Sac7d variant encoding sequence involves the PCR amplification of one fragment and a linearized vector. pFUSE-CHIg-hIG1 was linearized by PCR amplification with the forward oligonucleotide oligoCH-1 (SEQ ID NO: 16) and reverse oligonucleotide IL2ss_Rev (SEQ ID NO: 23) according to the PCR program 3. The DNA sequence coding the variable domain was amplified by PCR with the forward oligonucleotide OligoCH-6 (SEQ ID NO: 25) and reverse oligonucleotide OligoCH-3 (SEQ ID NO: 19) according to the PCR program 2.

The PCR products were then verified on a 1.5% (variable fragment amplified sequences and Sac7d variant amplified sequences) and 0.8% (linearized plasmids) agarose gel containing Gel Green nucleic acid stain (1×) and the bands of interest were cut under UV light and purified using the Wizard SV gel and PCR clean up system kit (Promega). To increase the amount of insert produced, a second PCR was performed on 5 ng of the purified variable fragment PCR products (4 replicates) using the same PCR mix and program. After a size verification of the bands on a 1.5% agarose gel, the same reactions were pooled and purified using the Wizard SV gel and PCR clean up system kit (Promega). PCR program 1: 98° C. for 30 sec, 25 cycles of denaturation (98° C. for 10 sec), annealing (60° C. for 30 sec) and elongation (72° C. for 2 min), then 72° C. for 5 min and allow to cool down at 14° C.

PCR Program 2: 98° C. for 30 sec, 25 cycles of denaturation (98° C. for 10 sec), annealing (60° C. for 30 sec) and elongation (72° C. for 30 sec), then 72° C. for 5 min and allow to cool down at 14° C.

PCR program 3: 98° C. for 30 sec, 25 cycles of denaturation (98° C. for 10 sec), annealing (69° C. for 30 sec) and elongation (72° C. for 2 min), then 72° C. for 5 min and allow to cool down at 14° C.

These PCRs allowed the formation of double stranded DNA with overlapping ends allowing their directional annealing by Gibson Assembly. A 20 µL Gibson Assembly mix containing 125 ng of DNA fragment with an insert/linearized plasmid molar ratio of 5, T5 exonuclease (0.08U, New England Biolabs), DNA Phusion polymerase (0.5U, New England Biolabs) and Taq DNA ligase (80U, New England Biolabs) in ISO 1× buffer was prepared. A one-hour incubation at was used for the Gibson Assembly to occur (Gibson et al., 2009)

The resulting ligated vectors were transformed in E. coli strain BL21(DE3)pLysS. An exponential cell culture ($OD_{600nm}$ 0.5) of BL21(DE3)pLysS competent cells (Coger) was transformed by heat shock with 10 µL of the above Gibson assembly reactions and controls. The cells were plated on 2YT agar medium at pH 7.5 containing Chloramphenicol (10 µg/mL, Sigma-Aldrich) and Zeocin (25 µg/mL, InvivoGen). Mini preparations were done using the Pure Yield Plasmid Minprep System (Promega) and a sample of each clone was stored in 20% glycerol at −80° C. Sequences were then validated by Sanger sequencing.

Example 2. Fusion to the Light Chain (N or C-Terminus)

The description is provided for the construction of the full light chains.

The strategy for the preparation of the full light chains followed the description of the preparation of the heavy chains except for the oligonucleotides named oligoCH-1 to 7 which were replaced by the respective oligonucleotides named oligoCL-1 to 7: oligoCL-1 (AAACGTACGGTGGCTGCACCA, SEQ ID NO: 28), oligoCL-2 (GGTAGTGCAGGCTCCGGCAGTGGCGGTAGCGA-CATCCAGATGAC-ACAGTC, SEQ ID NO: 29), oligoCL-3 (AGCCACCGTACGTTTTATCT, SEQ ID NO: 30), oligoCL-4 (TAGAGGGAGCTAGCTCGACATG, SEQ ID NO: 31), oligoCL-5 (GGAGCCTGCACTACCG-GAACCGCCTGAACCACACTCTCCCCTGTTGAAG, SEQ ID NO: 32), oligoCL-6 (CTTGTCACGAATTCAGA-CATCCAGA, SEQ ID NO: 33), oligoCL-7 (AGCTAGCTCCCTCTATTTCTCGCGTTCCGC, SEQ ID NO: 34) and the use of the pFUSE2ss-CLlg-hk instead of the pFUSE-CHIg-hIG1. Additionally, the transformation was made in the E. coli DH5α F'Iq strain with the following modifications: an exponential cell culture ($OD_{600nm}$ 0.5) of DH5α F'Iq competent cells (Life technologies) was transformed by heat shock with 10 µL of the Gibson assembly reactions. The cells were plated on 2YT agar medium at pH 8 containing Kanamycine (25 µg/mL, VWR) and Blasticidin (100 µg/mL, InvivoGen).

Example 3. Fusion of One NF to an Antibody (+Double Specificty)

HEK293-E6 cells were cultured in 1125 ml FreeStyle F17 medium supplemented with 4 mM of Glutamax and 0.1% of Pluronic F-68, at 37° C. and 110 rpm in a humidified atmosphere with 5% CO2. Transfections were performed as follows: when cell density reached 1.5-2×106 cells/ml, cells were transfected with a total of 1 mg DNA/L of the different plasmid pairs complexed with Polyethylenimine (PEI, polysciences ref 23966) in a DNA: PEI ratio of 1:2 and HC:LC ratio of 2:3. 6 hours post-transfection each culture was supplemented with ultra-low IgG fetal bovine serum and valproic acid. At 5 days post-transfection the culture supernatants were harvested by centrifugation at 2.000 g's for 20 min at 4° C. Culture supernatants were filtered through 0.2 µm and were loaded into Hitrap Protein A HP 5 ml columns (GE healthcare) previously equilibrated with PBS+500 mM NaCl pH 7.2 binding buffer. Elution was performed with 0.1 M of Citric Acid buffer at pH 3.0, fractions were neutralized with TRIS buffer pH 9.0, the product containing fractions were pooled together and injected into Superdex 200 2660 gel filtration column. The fractions containing the products at retention volumes of 150-160 ml were pooled together and concentrated up to 1-2 mg/ml using vivapsin centrifugal devices with 50 kDa membrane cut off.

Downstream purification of full IgG antibodies is well established process that usually involves an affinity chromatography step on protein A column.

The possibility to capture the different bi-specific antibodies made by the fusion of a Sac7d variant at either the N- or C-terminus of either the heavy or light chain, was demonstrated by biolayer interferometry on octet RED96.

Figures 2, 3:
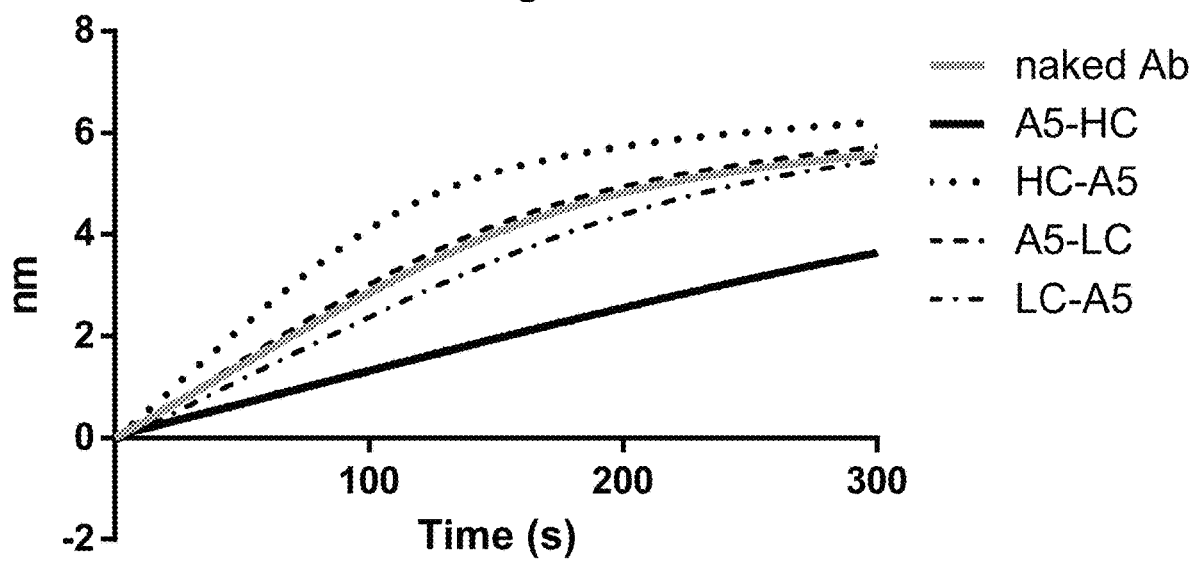
FIG. 2: alignment of the following proteins of the Sac7d family, A4YEA2-Mse7, DBP7_Sulfolobus_tokodaii, F4FYY6_Mcu7, SSo7d_Sulfolobus_solfataricus, Sac7d_Sulfolobus-acidocaldarius, Sac7e_Sulfolobus_acidocaldarius, Sis7a_Sulfolobus_islandicus, Sis7a_Sulfolobus_islandicus_1, Sis7a Sulfolobus isladicus_2, Ssh7a_Sulfolobus_shibatae, Ssh7b_Sulfolobus_shibatae, f4b8x5_Aho7c, f4b991_Aho7a, f4b9i5_Aho7b, and q96x56_Sto7, which have SEQ ID NOs. SEQ ID NO: 10, SEQ ID NO: 6, SEQ ID NO: 11, SEQ ID NO: 2, SEQ ID NO: 1, SEQ ID NO: 3, SEQ ID NO: 7, SEQ ID NO: 8, SEQ ID NO: 9, SEQ ID NO: 5, SEQ ID NO: 4, SEQ ID NO: 14, SEQ ID NO: 12, SEQ ID NO: 13, SEQ ID NO: 14, SEQ ID NO: 15, and SEQ ID NO: 43, respectively.
FIG. 3: loading of protein A biosensors on octet RD96 with antibody-Sac7d variant constructs. A5-HC: Sac7D variant at the N-term of heavy chain. HC-A5: Sac7D variant at the C-term of heavy chain. A5-LC: Sac7D variant at the N-term of light chain. LC-A5: Sac7D variant at the C-term of light chain. Naked antibody: control antibody.

Protein A biosensors were loaded for 300 sec with either of the four bi-specific constructs at 25 nM. All the steps were performed at 30° C. in TBS (Tris 20 mM, NaCl 150 mM, pH 7.4) supplemented with 0.01% of BSA and 0.002% of tween 20 with shaking at 1000 rpm. In all the cases, a fast capture was observed without trace of dissociation reflecting the stability of the binding (FIG. 3).

Example 4. Fusion of One NF to an Antibody: Binding to the Target of Either the Antibody or the Sac7d Variant The ability of the antibody and the Sac7d variant to bind their respective target when engaged in bi-specific constructions by the genetic fusion of the Sac7d variant at either the N- or C-terminus of either the heavy or light chain of the antibody, was demonstrated by biolayer interferometry on octet RED96 (Fortebio).

The bi-specific constructions were loaded on protein A sensors (Fortebio). After 180 sec of baseline, association and dissociation were allowed to occur respectively for 300 sec and 900 sec. All the steps were performed at 30° C. in TBS (Tris 20 mM, NaCl 150 mM, pH 7.4) supplemented with 0.01% of BSA and of tween 20 with shaking at 1000 rpm. A concentration range of 150 nM, 125 nM, 100 nM, 75 nM and 50 nM was used for the Sac7d variant target. A concentration range of 600 nM, 200 nM, 66.66 nM, 22.22 nM, 7.40 nM, 2.46 nM, and 0.82 nM was used for the antibody target. After each run, the sensors were regenerated by 3 cycles of glycine 10 mM pH2 (10 sec) and TBS (10 sec).

Figure 4:
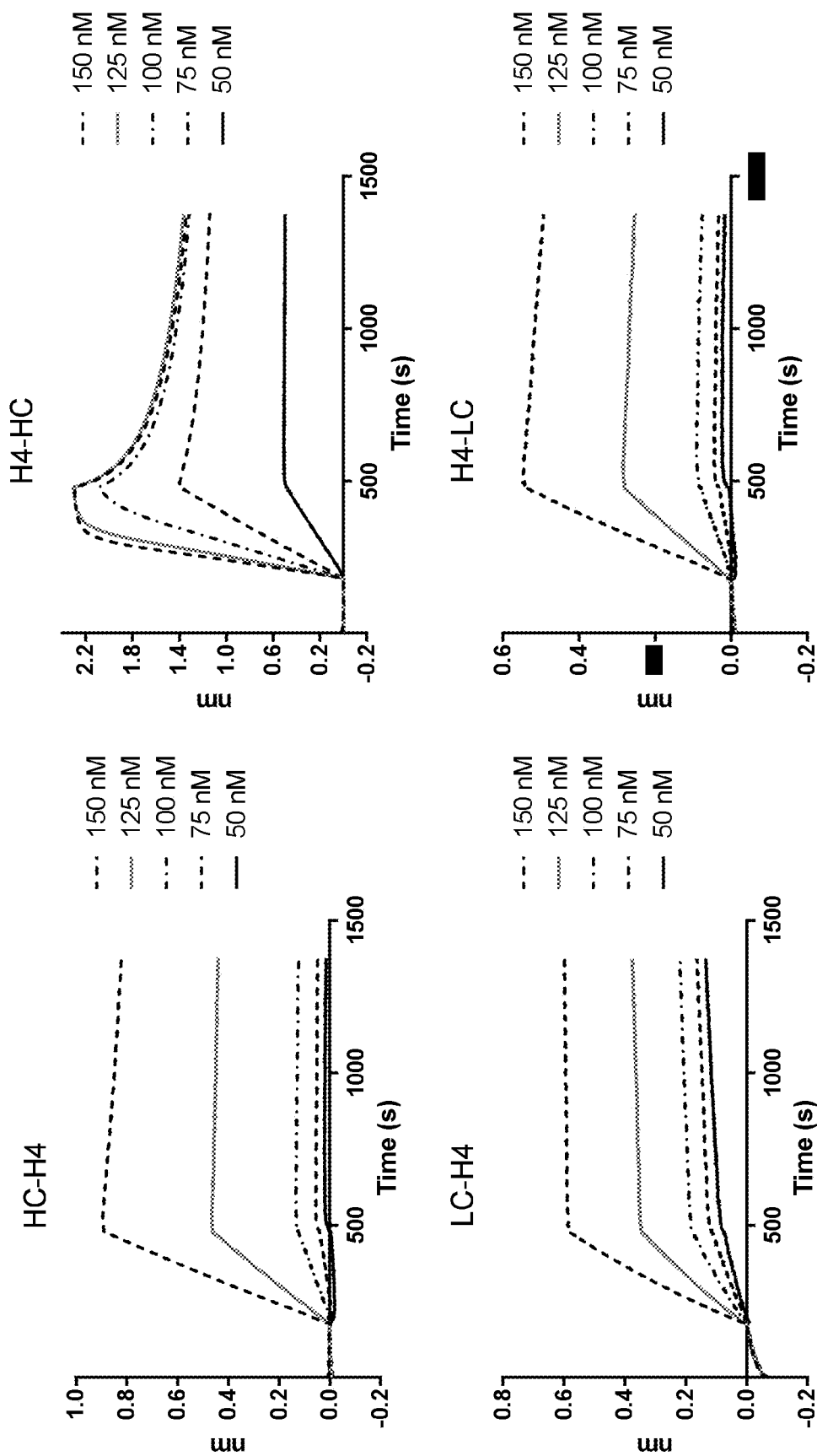
FIG. 4: Illustration of the functionality of the antibody when fused to the Sac7d variant (H4) at either the N- or C-terminus of either the heavy (HC) or light chain (LC). HC-H4: Sac7D variant at the C-term of heavy chain. H4-LC: Sac7D variant at the N-term of light chain. LC-H4: Sac7D variant at the C-term of light chain.
Figure 5:
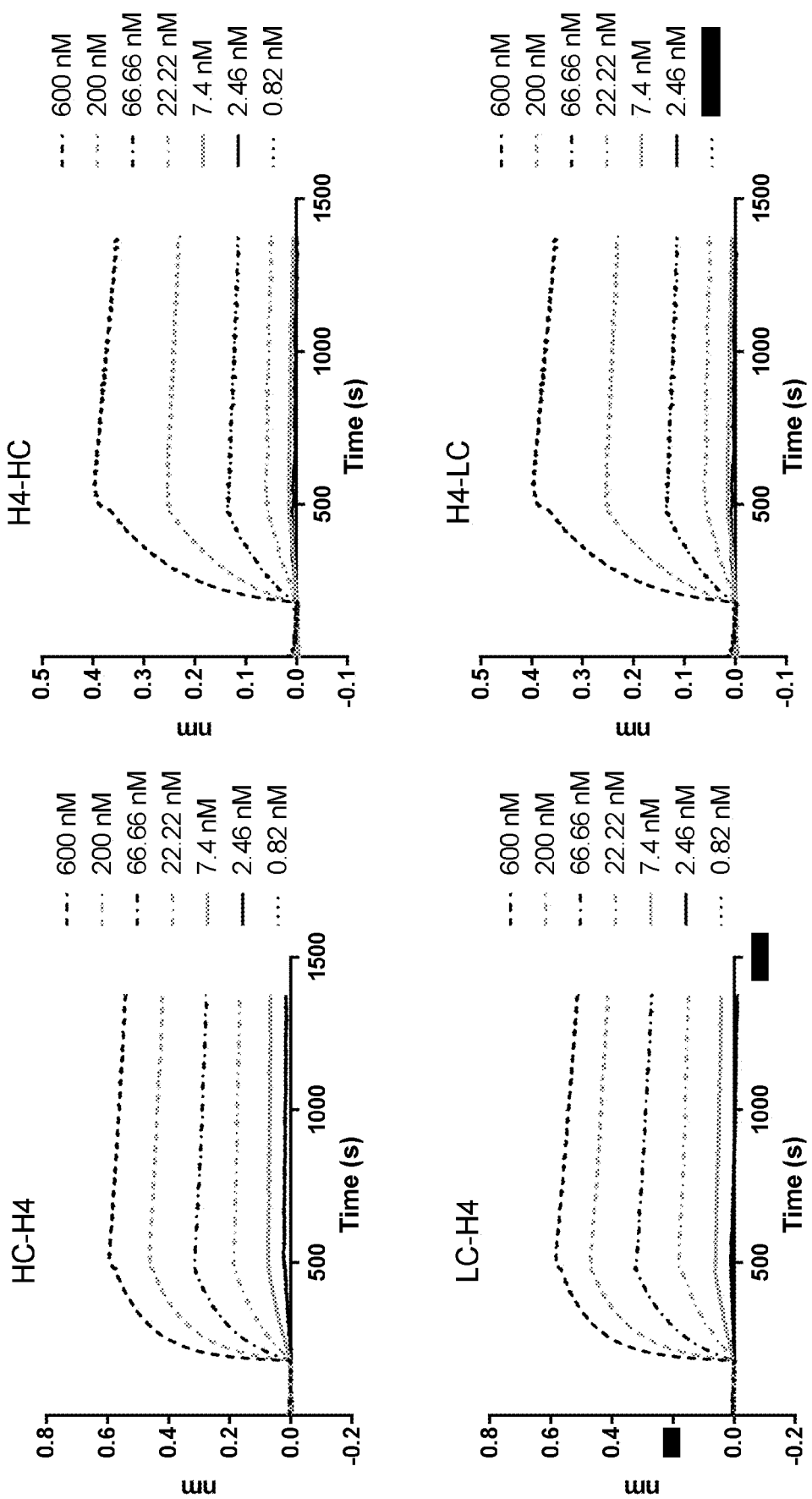
FIG. 5: illustration of the functionality of the Sac7d (H4) variant when fused to the antibody at either the N- or C-terminus of either the heavy (HC) or light chain (LC). HC-H4: Sac7D variant at the C-term of heavy chain. H4-LC: Sac7D variant at the N-term of light chain. LC-H4: Sac7D variant at the C-term of light chain.

Both the antibody and the Sac7d variant remained fully functional when linked together, regardless of the location of the fusion (FIGS. 4 and 5).

Example 5. Fusion of One NF to an Antibody: Double Specifity

One of the advantages of bi-specific molecules relies in their ability to bind simultaneously two different targets at a time.

The ability of the Sac7d variant and the antibody to simultaneously bind their respective target was demonstrated by biolayer interferometry on octet RED96. The bi-specific constructions were loaded on protein A sensors (Fortebio). After 180 sec of baseline, a 300 sec association time with the antibody target (200 nM) was performed followed by a 300 sec association time with the Sac7d variant target (300 nM). All the steps were performed at 30° C. in TBS (Tris 20 mM, NaCl 150 mM, pH 7.4) supplemented with 0.01% of BSA and 0.002% of tween 20 with shaking at 1000 rpm.

Figure 6:
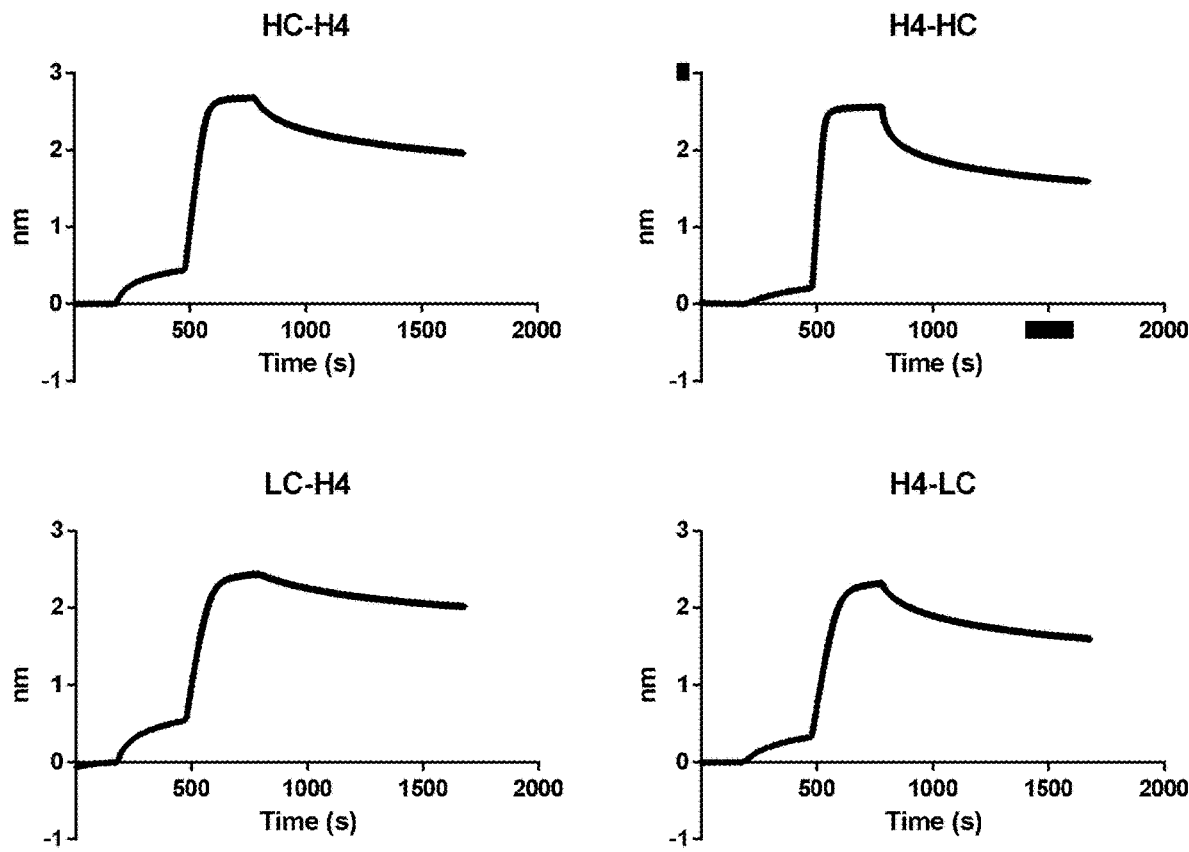
FIG. 6: Illustration of the dual binding capacity of the different bi-specific constructions by biolayer interferometry on octet RED96. HC-H4: Sac7D variant at the C-term of heavy chain. H4-LC: Sac7D variant at the N-term of light chain. LC-H4: Sac7D variant at the C-term of light chain.

FIG. 6 shows that Sac7d variant and the antibody simultaneously bind their respective target.

Example 6. Increase of Production or Same Production than Antibody without NF

The final productivity, corresponding to the amount of product obtained after all purification steps, was measured.

Figure 7:
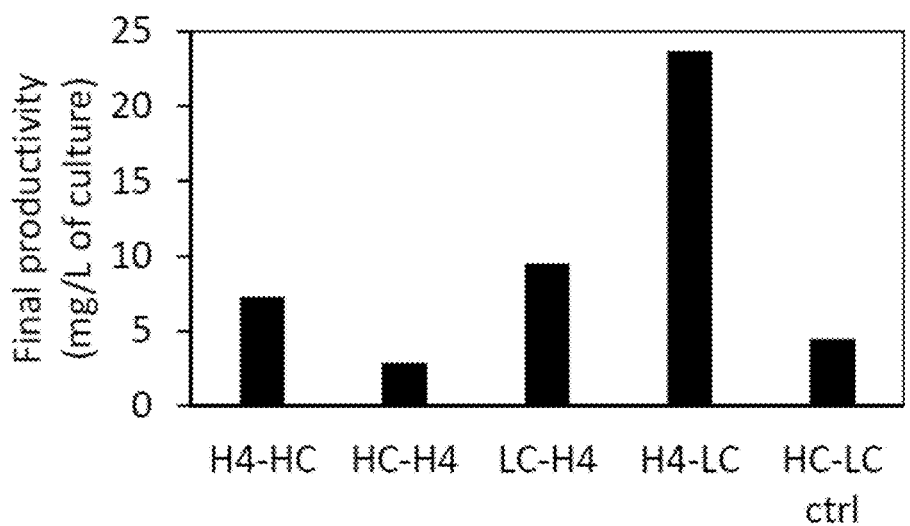
FIG. 7: illustration of the final productivity (total yield) for various constructs. H4-HC: Sac7D variant at the N-term of heavy chain. HC-H4: Sac7D variant at the C-term of heavy chain. H4-LC: Sac7D variant at the N-term of light chain. LC-H4: Sac7D variant at the C-term of light chain. HC-LC ctrl: control antibody.

FIG. 7 shows that the amount of recovered product was similar, or even better than that obtained for the antibody only.

Example 7. Fusion of More than One NF to an Antibody (to Obtain More than Two Specificities)

Construction of multi-specific molecules is performed according to the strategy describes above for bispecific molecules.

A further used of one PCR amplified DNA encoding fragment of Sac7d variant per extra specificity is made, so as to add it to the final molecule in the Gibson Assembly mix.

Linkers and overlapping matching end necessary for the Gibson Assembly are carried on the forward and reverse oligonucleotides and added to the Sac7d variant encoding sequence during the PCR amplification step. The multi-specific molecules are purified as in example 3.

Example 8. Production of Complexes in CHO-K1 (AFG) Cells

Chinese Hamster Ovary cells (CHO-K1, ATCC CCL-61) were cultured in F-12K medium with 1% L-glutamine and supplemented with 10% (v/v) deactivated ultra-low IgG foetal bovine serum and 1% (v/v) penicillin—streptomycin. The cells were expanded in tissue culture dishes and kept at 37° C. in a humidified constant atmosphere of 95% air and 5% CO2.

The day before transfection, cells were trypsinized and counted using erythrosine B 0.2% 1:1 (v/v). Cells were seeded at 126.4×106 cells per 10-layer Cell Culture Factory to be 70-90% confluent at the time of transfection.

For each cell factory, 2 mg of DNA (1.2 mg of LC and 0.8 mg of HC) was diluted in 200 mL of Opti-MEM® I Reduced Serum Medium. Then 2 mL of Polyethylenimine (PEI, linear MW 25,000) at 2 mg/mL was added and the mixture was allowed to incubate for 25 minutes at room temperature. Cells were transfected by adding the DNA/PEI complexes to fresh complete growth medium. 24 h after transfection, the media was changed for F-12K complete growth medium supplemented with antibiotics (blasticidin (10 µg/mL) and zeocin (300 µg/mL)) and valproic acid (0.5 mM final). Seven days after transfection, supernatants were collected and protein concentration was quantified by biolayer interferometry technology on protein-A biosensors according to standard established with naked antibody.

The production yield was compared with two commercial and therapeutic antibodies (Adalimumab and Infliximab). Genetic constructs were made in order to produce the heavy chain of these antibodies fused to a variant of a Sac7d protein, which possesses 12 mutations in the binding domain of the protein. The variant was present in N- or C-terminus of the heavy chain of Adalimumab and in N-terminus of the heavy chain of Infliximab.

Figure 8:
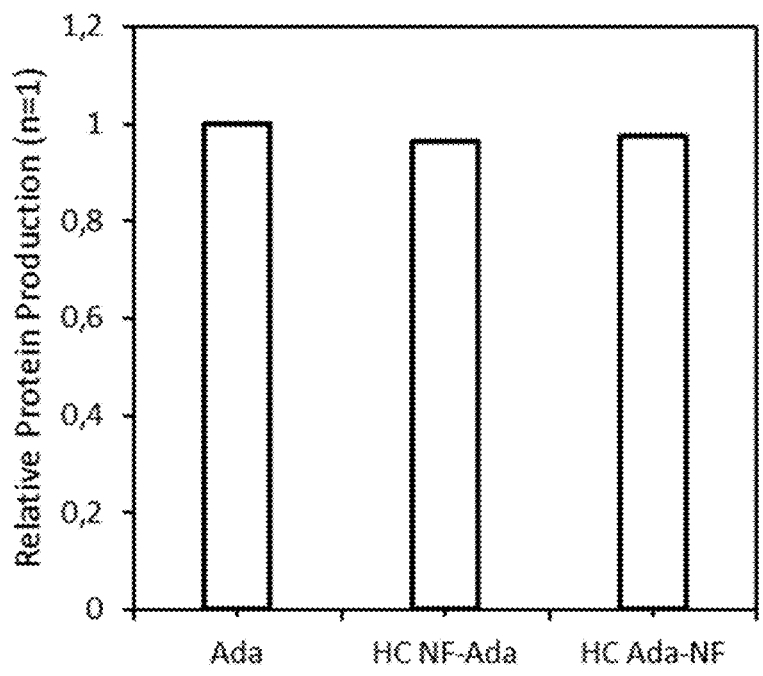
FIG. 8: Relative protein production of different antibody chimeras (with a Sac7d variant against IL17) compared to the naked antibodies (A) Adalimumab and (B) Infliximab.
Figure 8:
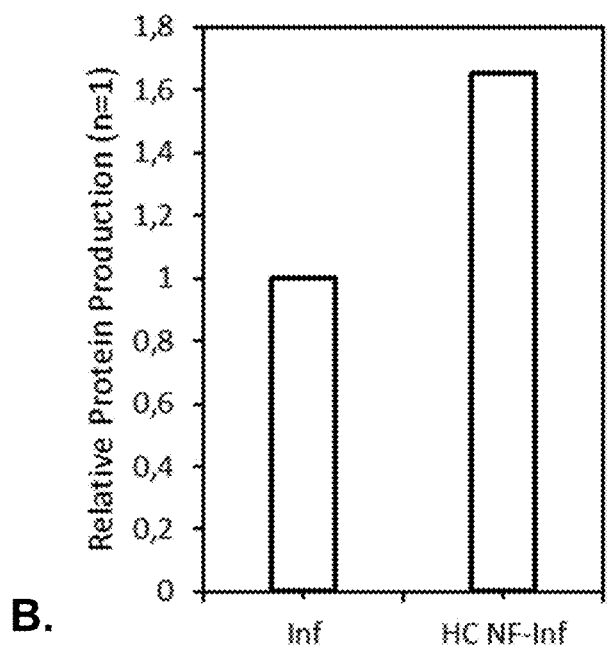

FIG. 8 shows that the yield of recovered polypeptide is maintained or increased for the chimeras containing the variant fused either in N- or C-terminus of the heavy chains for both (A) Adalimumab and (B) Infliximab.

Example 9. Use of the SHuffle (AFG) Technique

Complex proteins such as antibodies that are sensitives to oxidative stress and that require post translational modifications for their effector functions have been for long only manufactured in eukaryotic expression hosts such as the mammalian cell lines HEK293, CHO, and yeast. More recently, engineered bacterial strains such as the SHuffle were also demonstrated to be amenable for the intracellular manufacturing of functional antibodies, also named cyclonals.

The manufacturing of a chimera formed with an antibody (Adalimumab) and a variant of the Sac7d protein (Nanofitin) was investigated in the SHuffle expression host using a bicistronic vector as described by Robinson et al. (Nature Comm., 2015; 6:8072).

The naked antibody and three different antibody-Nanofitin chimeras were constructed, with the Nanofitin fusion either at the N-terminus of the light chain, C-terminus of the light chain or C-terminus of the heavy chain.

For all the antibody-Nanofitin chimera, a sequence coding for a 15 mer linker was inserted between the Nanofitin and the antibody DNA sequences.

Competent T7 SHuffle express pLysY were grown at 37° C. in 2YT medium supplemented with chloramphenicol (10 µg/mL). The culture was aliquoted into 1 mL fractions at OD 600 nm between 0.4-0.5 and centrifuged for 5 min at 4500 g. Pellets were resuspended with 200 µL of cold TSS buffer, then incubated on ice for 30 min upon addition of 0.5 µL of the expression vector to be transformed. The suspension was heat shocked for 30 sec at 42° C. followed by 5 min on ice.

The suspension was complemented with 800 μL of 2YT medium and incubated at 37° C. with continuous shaking at 200 rpm. After 1 hour, the suspension was centrifuged for 5 min at 4500 g. The pellet was resuspended with 20 μL of 2YT medium and the bacterias were spread on plate filled with 2YT-agar supplemented with chloramphenicol (10 μg/mL) and ampicilline (100 μg/mL). The plate was incubated overnight at 37° C.

10 mL of 2YT medium supplemented with chloramphenicol (10 μg/mL), ampicilline (100 μg/mL) and glucose 1% were inoculated with a single colony. The pre-culture was incubated overnight at 37° C. with continuous shaking at 200 rpm. 200 mL of 2YT medium supplemented with chloramphenicol (10 μg/mL), ampicilline (100 μg/mL) and glucose 0.1% were then inoculated with the 10 mL of pre-culture. The culture was incubated at 30° C. with continuous shaking at 200 rpm until OD 600 nm reached 0.7-0.8. Protein production was then triggered by addition of IPTG (1 mM final) and the cultured was maintained at 30° C. with shaking at 200 rpm for 16 additional hours. The culture was stopped by centrifugation for 30 min at 3214 g at 4° C. The pellet was resuspended with lysis buffer (PBS1X, 5 mM EDTA, Bugbuster® 1×, 5 μg/mL de DNase I) and incubated for 1 hour with shaking at 200 rpm. Cell debris were then pelleted by centrifugation for 45 min at 3220 g at 4° C. The lysis supernatant was collected.

Expressed antibodies chimeras were isolated by affinity chromatography on protein A resin (Pierce protein A agarose, ThermoFisher Scientific). 200 μL of 50% resin slurry was applied on a disposable 10 mL polypropylene column. The resin was washed with 10 column volumes of water and equilibrated with 10 column volumes of PBS (phosphate buffer saline, sigma-aldrich, P4417). Lysis supernatant was applied to the column which was then washed with 10 column volumes of PBS supplemented with 5 mM EDTA. 0.1 M Glycine pH 2-3 was used for the elution. Elution was collected by 100 μL fractions that were immediately neutralized by addition of 10 μL of Tris 1M (pH 8.8). The quantity of material recovered was then assessed by spectrophotometry at 280 nm. Purity of the samples was evaluated on 10% SDS-PAGE gel under reducing condition.

In this production system, the production yield of the chimeras is sensibly similar to the production yield of the naked antibodies (there is no significant difference between the obtained yields).

Furthermore, evaluation of the dual binding of the Nanofitin-Antibody chimera by biolayer interferometry showed that the antibody and the Sac7d variant maintain their affinity binding. To do this, protein A biosensor were loaded at 1.5 nm with different Nanofitin-Antibody chimeras and successively incubated for 420 sec with TNFalpha (20 nM) and IL17 (125 nM), followed by a dissociation phase (900 sec).

---

SEQUENCE LISTING

```
<160> NUMBER OF SEQ ID NOS: 43

<210> SEQ ID NO 1
<211> LENGTH: 66
<212> TYPE: PRT
<213> ORGANISM: Sulfolobus acidocaldarius

<400> SEQUENCE: 1

Met Val Lys Val Lys Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 2
<211> LENGTH: 64
<212> TYPE: PRT
<213> ORGANISM: Sulfolobus solfataricus

<400> SEQUENCE: 2

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60
```

```
<210> SEQ ID NO 3
<211> LENGTH: 65
<212> TYPE: PRT
<213> ORGANISM: Sulfolobus acidocaldarius

<400> SEQUENCE: 3

Met Ala Lys Val Arg Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Met Asp Met Leu Ala Arg Ala Glu Lys Lys
    50                  55                  60

Lys
65

<210> SEQ ID NO 4
<211> LENGTH: 64
<212> TYPE: PRT
<213> ORGANISM: Sulfolobus shibatae

<400> SEQUENCE: 4

Met Val Thr Val Lys Phe Lys Tyr Lys Gly Glu Glu Lys Glu Val Asp
1               5                   10                  15

Thr Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 5
<211> LENGTH: 64
<212> TYPE: PRT
<213> ORGANISM: Sulfolobus shibatae

<400> SEQUENCE: 5

Met Ala Thr Val Lys Phe Lys Tyr Lys Gly Glu Glu Lys Gln Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 6
<211> LENGTH: 64
<212> TYPE: PRT
<213> ORGANISM: Sulfolobus tokodaii

<400> SEQUENCE: 6

Met Val Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Asp Asn Gly Lys Thr Gly Arg Gly Ala Val Ser Glu Lys
        35                  40                  45
```

```
Asp Ala Pro Lys Glu Leu Leu Gln Met Leu Glu Lys Ser Gly Lys Lys
        50                  55                  60
```

<210> SEQ ID NO 7
<211> LENGTH: 64
<212> TYPE: PRT
<213> ORGANISM: Sulfolobus islandicus

<400> SEQUENCE: 7

```
Met Val Thr Val Lys Phe Lys Tyr Lys Gly Glu Glu Lys Gln Val Asp
1               5                   10                  15

Thr Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
        50                  55                  60
```

<210> SEQ ID NO 8
<211> LENGTH: 64
<212> TYPE: PRT
<213> ORGANISM: Sulfolobus islandicus

<400> SEQUENCE: 8

```
Met Thr Thr Val Lys Phe Lys Tyr Lys Gly Glu Glu Lys Gln Val Asp
1               5                   10                  15

Thr Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
        50                  55                  60
```

<210> SEQ ID NO 9
<211> LENGTH: 64
<212> TYPE: PRT
<213> ORGANISM: Sulfolobus islandicus

<400> SEQUENCE: 9

```
Met Thr Thr Val Lys Phe Lys Tyr Lys Gly Glu Glu Lys Gln Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
        50                  55                  60
```

<210> SEQ ID NO 10
<211> LENGTH: 62
<212> TYPE: PRT
<213> ORGANISM: Metallosphaera sedula.

<400> SEQUENCE: 10

```
Met Ala Thr Lys Ile Lys Phe Lys Tyr Lys Gly Gln Asp Leu Glu Val
1               5                   10                  15

Asp Ile Ser Lys Val Lys Lys Val Trp Lys Val Gly Lys Met Val Ser
            20                  25                  30

Phe Thr Tyr Asp Asp Asn Gly Lys Thr Gly Arg Gly Ala Val Ser Glu
```

```
            35                  40                  45
Lys Asp Ala Pro Lys Glu Leu Leu Asn Met Ile Gly Lys Lys
    50                  55                  60

<210> SEQ ID NO 11
<211> LENGTH: 62
<212> TYPE: PRT
<213> ORGANISM: Metallosphaera cuprina

<400> SEQUENCE: 11

Met Ala Thr Lys Ile Lys Phe Lys Tyr Lys Gly Gln Asp Leu Glu Val
1               5                   10                  15

Asp Ile Ser Lys Val Lys Lys Val Trp Lys Val Gly Lys Met Val Ser
            20                  25                  30

Phe Thr Tyr Asp Asp Asn Gly Lys Thr Gly Arg Gly Ala Val Ser Glu
        35                  40                  45

Lys Asp Ala Pro Lys Glu Leu Leu Ser Met Ile Gly Lys Lys
    50                  55                  60

<210> SEQ ID NO 12
<211> LENGTH: 61
<212> TYPE: PRT
<213> ORGANISM: Acidianus hospitalis

<400> SEQUENCE: 12

Met Thr Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Glu Lys Leu Glu Lys Lys
    50                  55                  60

<210> SEQ ID NO 13
<211> LENGTH: 62
<212> TYPE: PRT
<213> ORGANISM: Acidianus hospitalis

<400> SEQUENCE: 13

Met Ala Thr Lys Val Lys Phe Lys Tyr Lys Gly Glu Glu Lys Glu Val
1               5                   10                  15

Asp Ile Ser Lys Ile Lys Lys Val Trp Arg Val Gly Lys Met Ile Ser
            20                  25                  30

Phe Thr Tyr Asp Asp Asn Gly Lys Thr Gly Arg Gly Ala Val Ser Glu
        35                  40                  45

Lys Asp Ala Pro Lys Glu Leu Leu Asp Lys Leu Glu Lys Lys
    50                  55                  60

<210> SEQ ID NO 14
<211> LENGTH: 60
<212> TYPE: PRT
<213> ORGANISM: Acidianus hospitalis

<400> SEQUENCE: 14

Met Ala Thr Lys Val Lys Phe Lys Tyr Lys Gly Glu Glu Lys Glu Val
1               5                   10                  15

Asp Ile Ser Lys Ile Lys Lys Val Trp Arg Val Gly Lys Met Ile Ser
            20                  25                  30
```

Phe Thr Tyr Asp Asp Asn Gly Lys Thr Gly Arg Gly Ala Val Ser Glu
            35                  40                  45

Lys Asp Ala Pro Lys Glu Leu Leu Glu Lys Leu Lys
        50                  55                  60

<210> SEQ ID NO 15
<211> LENGTH: 68
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (2)..(2)
<223> OTHER INFORMATION: Xaa is V, A or T
<220> FEATURE:
<221> NAME/KEY: VARIANT
<222> LOCATION: (3)..(3)
<223> OTHER INFORMATION: Xaa is T or K
<220> FEATURE:
<221> NAME/KEY: VARIANT
<222> LOCATION: (4)..(4)
<223> OTHER INFORMATION: Xaa is - or K
<220> FEATURE:
<221> NAME/KEY: VARIANT
<222> LOCATION: (6)..(6)
<223> OTHER INFORMATION: Xaa is R or K
<220> FEATURE:
<221> NAME/KEY: VARIANT
<222> LOCATION: (15)..(15)
<223> OTHER INFORMATION: Xaa is E or Q
<220> FEATURE:
<221> NAME/KEY: VARIANT
<222> LOCATION: (18)..(18)
<223> OTHER INFORMATION: Xaa is T or I
<220> FEATURE:
<221> NAME/KEY: VARIANT
<222> LOCATION: (31)..(31)
<223> OTHER INFORMATION: Xaa is V or I
<220> FEATURE:
<221> NAME/KEY: VARIANT
<222> LOCATION: (37)..(39)
<223> OTHER INFORMATION: Xaa Xaa Xaa is EGG or DN-
<220> FEATURE:
<221> NAME/KEY: VARIANT
<222> LOCATION: (57)..(57)
<223> OTHER INFORMATION: Xaa is M or L
<220> FEATURE:
<221> NAME/KEY: VARIANT
<222> LOCATION: (58)..(58)
<223> OTHER INFORMATION: Xaa is Q, D or E
<220> FEATURE:
<221> NAME/KEY: VARIANT
<222> LOCATION: (59)..(59)
<223> OTHER INFORMATION: Xaa is M or K
<220> FEATURE:
<221> NAME/KEY: VARIANT
<222> LOCATION: (61)..(67)
<223> OTHER INFORMATION: Xaa is -------, EKS--GK, EK---QK, ARAEREK,
    ARA-EKK, E-----K, EKS--G, ACAEREK oR ACA-EKK

<400> SEQUENCE: 15

Met Xaa Xaa Xaa Val Xaa Phe Lys Tyr Lys Gly Glu Glu Lys Xaa Val
1               5                   10                  15

Asp Xaa Ser Lys Ile Lys Lys Val Trp Arg Val Gly Lys Met Xaa Ser
            20                  25                  30

Phe Thr Tyr Asp Xaa Xaa Xaa Gly Lys Thr Gly Arg Gly Ala Val Ser
        35                  40                  45

Glu Lys Asp Ala Pro Lys Glu Leu Xaa Xaa Xaa Leu Xaa Xaa Xaa Xaa
    50                  55                  60

Xaa Xaa Xaa Lys
65

<210> SEQ ID NO 16
<211> LENGTH: 18
<212> TYPE: DNA
<213> ORGANISM: Artificial Sequence
<220> FEATURE:
<223> OTHER INFORMATION: oligonucleotide oligoCH-1

<400> SEQUENCE: 16
gctagcacca agggccca                                               18

<210> SEQ ID NO 17
<211> LENGTH: 24
<212> TYPE: DNA
<213> ORGANISM: Artificial Sequence
<220> FEATURE:
<223> OTHER INFORMATION: oligonucleotide VHfuse_Rev

<400> SEQUENCE: 17
tgaattcgtg acaagtgcaa gact                                        24

<210> SEQ ID NO 18
<211> LENGTH: 49
<212> TYPE: DNA
<213> ORGANISM: Artificial Sequence
<220> FEATURE:
<223> OTHER INFORMATION: oligonucleotide OligoCH-2

<400> SEQUENCE: 18
ggtagtgcag gctccggcag tggcggtagc gaggtgcagt tggtagagt             49

<210> SEQ ID NO 19
<211> LENGTH: 18
<212> TYPE: DNA
<213> ORGANISM: Artificial Sequence
<220> FEATURE:
<223> OTHER INFORMATION: OligoCH-3

<400> SEQUENCE: 19
gcccttggtg ctagcact                                               18

<210> SEQ ID NO 20
<211> LENGTH: 30
<212> TYPE: DNA
<213> ORGANISM: Artificial Sequence
<220> FEATURE:
<223> OTHER INFORMATION: oligonucleotide VH_NF_For

<400> SEQUENCE: 20
cttgtcacga attcagtcaa ggtgaaattc                                  30

<210> SEQ ID NO 21
<211> LENGTH: 45
<212> TYPE: DNA
<213> ORGANISM: Artificial Sequence
<220> FEATURE:
<223> OTHER INFORMATION: oligonucleotide Glink15.1_Rev

<400> SEQUENCE: 21
ggagcctgca ctaccggaac cgcctgaacc tttctcgcgt tccgc                 45

<210> SEQ ID NO 22
<211> LENGTH: 19
<212> TYPE: DNA
<213> ORGANISM: Artificial Sequence
<220> FEATURE:

<223> OTHER INFORMATION: oligonucleotide OligoCH-4

<400> SEQUENCE: 22
tgagtcctag ctggccaga                                          19

<210> SEQ ID NO 23
<211> LENGTH: 31
<212> TYPE: DNA
<213> ORGANISM: Artificial Sequence
<220> FEATURE:
<223> OTHER INFORMATION: oligonucleotide IL2ss_Rev

<400> SEQUENCE: 23
tgaattcgtg acaagtgcaa gacttagtgc a                            31

<210> SEQ ID NO 24
<211> LENGTH: 50
<212> TYPE: DNA
<213> ORGANISM: Artificial Sequence
<220> FEATURE:
<223> OTHER INFORMATION: Oligonucleotide OligoCH-5

<400> SEQUENCE: 24
ggagcctgca ctaccggaac cgcctgaacc tttacccgga gacaggdgaga        50

<210> SEQ ID NO 25
<211> LENGTH: 21
<212> TYPE: DNA
<213> ORGANISM: Artificial Sequence
<220> FEATURE:
<223> OTHER INFORMATION: oligonucleotide OligoCH-6

<400> SEQUENCE: 25
cttgtcacga attcagaggt g                                       21

<210> SEQ ID NO 26
<211> LENGTH: 45
<212> TYPE: DNA
<213> ORGANISM: Artificial Sequence
<220> FEATURE:
<223> OTHER INFORMATION: oligonucleotide Glink15.1_For

<400> SEQUENCE: 26
ggtagtgcag gctccggcag tggcggtagc gtcaaggtga aattc             45

<210> SEQ ID NO 27
<211> LENGTH: 30
<212> TYPE: DNA
<213> ORGANISM: Artificial Sequence
<220> FEATURE:
<223> OTHER INFORMATION: oligonucleotide OligoCH-7

<400> SEQUENCE: 27
gccagctagg actcatttct cgcgttccgc                              30

<210> SEQ ID NO 28
<211> LENGTH: 21
<212> TYPE: DNA
<213> ORGANISM: Artificial Sequence
<220> FEATURE:
<223> OTHER INFORMATION: oligoCL-1

<400> SEQUENCE: 28
aaacgtacgg tggctgcacc a                                       21

```
<210> SEQ ID NO 29
<211> LENGTH: 50
<212> TYPE: DNA
<213> ORGANISM: Artificial Sequence
<220> FEATURE:
<223> OTHER INFORMATION: oligoCL-2

<400> SEQUENCE: 29
ggtagtgcag gctccggcag tggcggtagc gacatccaga tgacacagtc          50

<210> SEQ ID NO 30
<211> LENGTH: 20
<212> TYPE: DNA
<213> ORGANISM: Artificial Sequence
<220> FEATURE:
<223> OTHER INFORMATION: oligoCL-3

<400> SEQUENCE: 30
agccaccgta cgttttatct                                           20

<210> SEQ ID NO 31
<211> LENGTH: 22
<212> TYPE: DNA
<213> ORGANISM: Artificial Sequence
<220> FEATURE:
<223> OTHER INFORMATION: oligoCL-4

<400> SEQUENCE: 31
tagagggagc tagctcgaca tg                                        22

<210> SEQ ID NO 32
<211> LENGTH: 49
<212> TYPE: DNA
<213> ORGANISM: Artificial Sequence
<220> FEATURE:
<223> OTHER INFORMATION: oligoCL-5

<400> SEQUENCE: 32
ggagcctgca ctaccggaac cgcctgaacc acactctccc ctgttgaag           49

<210> SEQ ID NO 33
<211> LENGTH: 25
<212> TYPE: DNA
<213> ORGANISM: Artificial Sequence
<220> FEATURE:
<223> OTHER INFORMATION: oligoCL-6

<400> SEQUENCE: 33
cttgtcacga attcagacat ccaga                                     25

<210> SEQ ID NO 34
<211> LENGTH: 30
<212> TYPE: DNA
<213> ORGANISM: Artificial Sequence
<220> FEATURE:
<223> OTHER INFORMATION: oligoCL-7

<400> SEQUENCE: 34
agctagctcc ctctatttct cgcgttccgc                                30

<210> SEQ ID NO 35
<211> LENGTH: 66
<212> TYPE: PRT
<213> ORGANISM: Artificial Sequence
<220> FEATURE:
<223> OTHER INFORMATION: Sequence binding to IL17
<220> FEATURE:
```

```
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid

<400> SEQUENCE: 35

Met Val Lys Val Lys Phe Xaa Xaa Xaa Gly Glu Glu Lys Glu Val Asp
1               5                   10                  15

Thr Ser Lys Ile Phe Asn Val Trp Arg Xaa Gly Lys Xaa Val Asn Phe
            20                  25                  30

Met Tyr Asp Asp Asn Gly Lys Ile Gly Ile Gly Xaa Val Xaa Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 36
<211> LENGTH: 66
<212> TYPE: PRT
<213> ORGANISM: Artificial Sequence
<220> FEATURE:
<223> OTHER INFORMATION: Sequence binding to IL17
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid

<400> SEQUENCE: 36

Met Val Lys Val Lys Phe Xaa Xaa Xaa Gly Glu Glu Lys Glu Val Asp
1               5                   10                  15

Thr Ser Lys Ile Phe Asn Val Trp Arg Xaa Gly Lys Ser Val Asn Phe
            20                  25                  30

Met Tyr Asp Asp Asn Gly Lys Ile Gly Ile Gly Xaa Val Xaa Glu Lys
        35                  40                  45

Asp Ala Pro Lys Glu Leu

```
<210> SEQ ID NO 37
<211> LENGTH: 66
<212> TYPE: PRT
<213> ORGANISM: Artificial Sequence
<220> FEATURE:
<223> OTHER INFORMATION: Sequence binding to IL17

<400> SEQUENCE: 37

Met Val Lys Val Lys Phe His Ala Lys Gly Glu Glu Lys Glu Val Asp
1               5                   10                  15

Thr Ser Lys Ile Phe Asn Val Trp Arg Ser Gly Lys Ser Val Asn Phe
            20                  25                  30

Met Tyr Asp Asp Asn Gly Lys Ile Gly Ile Gly His Val Asp Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 38
<211> LENGTH: 66
<212> TYPE: PRT
<213> ORGANISM: Artificial Sequence
<220> FEATURE:
<223> OTHER INFORMATION: Sequence binding to IL17

<400> SEQUENCE: 38

Met Val Lys Val Lys Phe Ser Arg Phe Gly Glu Glu Lys Glu Val Asp
1               5                   10                  15

Thr Ser Lys Ile Phe Asn Val Trp Arg Ile Gly Lys Thr Val Asn Phe
            20                  25                  30

Met Tyr Asp Asp Asn Gly Lys Ile Gly Ile Gly Ala Val Asp Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 39
<211> LENGTH: 65
<212> TYPE: PRT
<213> ORGANISM: Artificial Sequence
<220> FEATURE:
<223> OTHER INFORMATION: Sequence binding to TNF-alpha
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
```

```
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid

<400> SEQUENCE: 39

Met Val Lys Val Lys Phe Xaa Xaa Xaa Gly Xaa Glu Lys Glu Val Asp
1               5                   10                  15

Thr Ser Lys Ile Xaa Xaa Val Xaa Arg Xaa Gly Lys Xaa Val His Phe
            20                  25                  30

Trp Tyr Glu Asp Asn Gly Lys Ile Asp Lys Gly Xaa Val Xaa Glu Lys
        35                  40                  45

Asp Ala Pro Lys Glu Leu Leu Asp Met Leu Ala Arg Ala Glu Arg Glu
    50                  55                  60

Lys
65

<210> SEQ ID NO 40
<211> LENGTH: 65
<212> TYPE: PRT
<213> ORGANISM: Artificial Sequence
<220> FEATURE:
<223> OTHER INFORMATION: Sequence binding to TNF-alpha
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid

<400> SEQUENCE: 40

Met Val Lys Val Lys Phe Xaa Xaa Xaa Gly Xaa Glu Lys Glu Val Asp
1               5                   10                  15

Thr Ser Lys Ile Xaa His Val Met Arg Xaa Gly Lys Xaa Val His Phe
            20                  25                  30

Trp Tyr Glu Asp Asn Gly Lys Ile Asp Lys Gly Xaa Val Xaa Glu Lys
        35                  40                  45

Asp Ala Pro Lys Glu Leu Leu Asp Met Leu Ala Arg Ala Glu Arg Glu
    50                  55                  60

Lys
65
```

```
<210> SEQ ID NO 41
<211> LENGTH: 65
<212> TYPE: PRT
<213> ORGANISM: Artificial Sequence
<220> FEATURE:
<223> OTHER INFORMATION: Sequence binding to TNF-alpha

<400> SEQUENCE: 41

Met Val Lys Val Lys Phe Val Met Phe Gly Lys Glu Lys Glu Val Asp
1               5                   10                  15

Thr Ser Lys Ile Val His Val Met Arg Gln Gly Lys Leu Val His Phe
            20                  25                  30

Trp Tyr Glu Asp Asn Gly Lys Ile

6. The polypeptide of claim 5, wherein the other protein or polypeptide comprises another variant of an OB-fold protein derived from a Sac7d protein, wherein the other variant has between 4 and 20 or between 5 and 20 residues involved in the binding of said Sac7d protein with its native ligand mutated.

7. The polypeptide of claim 6, wherein the mutated amino acid residues correspond to amino acids selected from V2, K3, K5, K7, Y8, K9, G10, E11, K13, E14, T17, K21, K22, W24, V26, G27, K28, M29, S31, T33, Y34, D35, D36, N37, G38, K39, T40, G41, R42, A44, S46, E47, K48, D49, A50 and P51 of the Sac7d protein set forth in SEQ ID NO: 1.

8. The polypeptide of claim 6, wherein the other variant binds to TNF-alpha.

9. The polypeptide of claim 5, wherein the other protein is an antibody.

10. The polypeptide of claim 9, wherein the variant OB-fold polypeptide is fused to two heavy chains or to two light chains of the antibody.

11. The polypeptide of claim 9, wherein the variant OB-fold polypeptide is fused to one heavy chain and to one light chain of the antibody.

12. The polypeptide of claim 6, wherein the variant OB-fold polypeptide and the other variant of the OB-fold protein derived from the Sac7d protein are fused to the heavy chains and/or to the light chains of an antibody.

13. The polypeptide of claim 9, wherein the antibody is a therapeutic antibody.

14. The polypeptide of claim 9, wherein the antibody binds to a protein selected from TNFalpha, IL23, IL12, IL4, IL13, IL31, the receptor of IL31, and a tumor specific antigen.

15. The polypeptide of claim 1, which is conjugated to an organic molecule.

16. A genetic construct comprising a DNA sequence coding for the polypeptide of claim 1.

17. A genetic construct comprising a DNA sequence selected from:
    (a) a sequence coding for a heavy chain of an antibody fused, at its 3' end, with a sequence coding for the polypeptide of claim 1;
    (b) a sequence coding for a heavy chain of an antibody fused, at its 5' end, with a sequence coding for the polypeptide of claim 1;
    (c) a sequence coding for a light chain of an antibody fused, at its 3' end, with a sequence coding for the polypeptide of claim 1; and
    (d) a sequence coding for a light chain of an antibody fused, at its 5' end, with a sequence coding for the polypeptide of claim 1.

18. A vector comprising the genetic construct of claim 16.

19. A host cell comprising the genetic construct of claim 16.

20. A method for producing the polypeptide of claim 1, comprising:
    (a) culturing a cell culture, wherein the cells have been transformed by a genetic construct comprising a DNA sequence coding for the polypeptide of claim 1, and
    (b) recovering the polypeptide.

* * * * *